(12) United States Patent
Svoboda et al.

(10) Patent No.: US 11,395,904 B2
(45) Date of Patent: Jul. 26, 2022

(54) CATHETER TUBE

(71) Applicants: RIOCATH MEDICAL DEVICES, A.S., Prague (CZ); USTAV ORGANICKE CHEMIE A BIOCHEMIE AV CR, V.V.I., Prague (CZ)

(72) Inventors: Miroslav Svoboda, Prague (CZ); Vit Pokorny, Prague (CZ)

(73) Assignees: RIOCATH MEDICAL DEVICES, A.S., Prague (CZ); USTAV ORGANICKE CHEMIE A BIOCHEMIE AV CR, V.V.I., Prague (CZ)

(*) Notice: Subject to any disclaimer, the term of this patent is extended or adjusted under 35 U.S.C. 154(b) by 274 days.

(21) Appl. No.: 16/328,772

(22) PCT Filed: Aug. 30, 2017

(86) PCT No.: PCT/EP2017/071784
§ 371 (c)(1),
(2) Date: Feb. 27, 2019

(87) PCT Pub. No.: WO2018/041903
PCT Pub. Date: Mar. 8, 2018

(65) Prior Publication Data
US 2019/0240456 A1 Aug. 8, 2019

(30) Foreign Application Priority Data
Aug. 31, 2016 (EP) .................................. 16186631

(51) Int. Cl.
*A61M 25/00* (2006.01)
*A61M 25/01* (2006.01)
(Continued)

(52) U.S. Cl.
CPC .... *A61M 25/0119* (2013.01); *A61M 25/0009* (2013.01); *A61M 25/0013* (2013.01);
(Continued)

(58) Field of Classification Search
CPC .......... A61M 25/0119; A61M 25/0013; A61M 25/0054; A61M 25/0194; A61M 25/0029;
(Continued)

(56) References Cited

U.S. PATENT DOCUMENTS 1,596,754 A * 8/1926 Moschelle ............ A61M 27/00
604/541
3,908,635 A 9/1975 Vick
(Continued)

OTHER PUBLICATIONS

International Search Report and Written Opinion for corresponding PCT application No. PCT/EP2017/071784, dated Nov. 14, 2017.

*Primary Examiner* — Nathan R Price
*Assistant Examiner* — Tania Ismail
(74) *Attorney, Agent, or Firm* — Notaro, Michalos & Zaccaria P.C.

(57) ABSTRACT

A catheter that has a catheter tube everting inside-out during the process of catheterization. The catheter tube has a plurality of longitudinal protrusions extending from the first end of the catheter tube through at least a portion of the catheter tube, and forming an angle of 0 degrees to 45 degrees with respect to the longitudinal axis of the catheter tube and facing radially inwards, and provides for dilating a circumference of the catheter tube upon everting the catheter tube inside-out from the first end of the catheter tube.

19 Claims, 14 Drawing Sheets

(51) Int. Cl.
- *B29C 48/00* (2019.01)
- *B29C 48/09* (2019.01)
- *B29C 48/21* (2019.01)
- *B29D 23/00* (2006.01)
- *A61F 2/966* (2013.01)
- *A61F 2/962* (2013.01)
- *A61F 2/82* (2013.01)
- *B33Y 80/00* (2015.01)

(52) U.S. Cl.
CPC ..... *A61M 25/0054* (2013.01); *B29C 48/0022* (2019.02); *B29C 48/09* (2019.02); *B29C 48/21* (2019.02); *B29D 23/00* (2013.01); *A61F 2/962* (2013.01); *A61F 2/966* (2013.01); *A61F 2002/821* (2013.01); *A61M 25/0023* (2013.01); *A61M 25/0029* (2013.01); *A61M 25/0194* (2013.01); *A61M 2025/0024* (2013.01); *A61M 2025/0046* (2013.01); *A61M 2025/0062* (2013.01); *A61M 2205/0266* (2013.01); *B33Y 80/00* (2014.12)

(58) Field of Classification Search
CPC ...... A61M 25/0023; A61M 2025/0024; A61M 2025/0062; A61M 2025/0046; A61F 2002/821; A61F 2/966; A61F 2/962; A61F 2/25

See application file for complete search history.

(56) References Cited

U.S. PATENT DOCUMENTS

| | | | |
|---|---|---|---|
| 4,871,358 A | | 10/1989 | Gold |
| 5,176,659 A | * | 1/1993 | Mancini ............ A61M 25/0023 604/164.1 |
| 5,279,280 A | | 1/1994 | Bacich et al. |
| 5,902,286 A | | 5/1999 | Reitz |
| 9,028,401 B1 | | 5/2015 | Bacich et al. |
| 2002/0133127 A1 | | 9/2002 | Collins |
| 2006/0173525 A1 | | 8/2006 | Behl et al. |
| 2011/0251595 A1 | * | 10/2011 | Kassab ............. A61M 25/0054 604/528 |
| 2018/0021481 A1 | * | 1/2018 | Yin .................. A61M 25/0136 206/364 |

* cited by examiner

CATHETER TUBE

TECHNICAL FIELD

The present invention relates to a catheter, which comprises a catheter tube everting inside-out during the process of catheterization.

BACKGROUND ART

The term catheter is applied to a generally tubular instrument, which is inserted into a body cavity, for the purpose of drainage, administration of fluids or gases, or accessing the body tissue by surgical instruments in a controlled manner. Catheters may perform other tasks depending on the type of catheter.

To date, the most widely used catheter has been the Foley catheter, invented by Dr. Frederick Foley around 1945. The conventional Foley catheter has several drawbacks, for instance, once a conventional catheter, is removed from its sterile package before its application, the exterior surface, which will be in contact with body tissue, is often exposed to non-sterile environment, or it tends to drag bacteria and other debris along the surface of the body cavity as the tube is being pushed in. This increases the likelihood of bacteria spreading along the length of the channel, possibly causing infection, which is probably the most serious health problem arising from the use of conventional catheter.

Apart from that, the insertion of the conventional catheter is slow, difficult, unsecure and painful, because during the catheterization, the body tissue inside the body cavity may be strongly irritated and traumatized. All the drawbacks of the conventional catheter are well described in the U.S. Pat. No. 4,871,358, which discloses a medical catheter using an externally-based inversionary tube, designed to allow the outer surface of the tube, which is adjacent to body tissue, to remain stationary relative to that tissue during advancement and retraction of the catheter. This is ensured by the construction of the tube, the tube being everted onto itself at a fold to define inner and outer tube portions. The inner tube portion resides within said outer tube portion and is slidably moveable into and out of said outer tube portion in an axial direction. When a force is applied by the user onto the inner portion of the catheter tube in the axial direction towards the fold, the force is axially transmitted through the inner portion of the catheter tube to the fold and resolves into radially outward force, which when of sufficient magnitude, transforms the inner portion of the tube into the outer portion of the tube. The relative lengths of said outer and inner tube portions are changed and the position of said fold is shifted further into the body cavity. The problem with this construction is that it does not provide a catheter of sufficient length for a real life usage.

There are several forces acting in the system. First, there is a force applied by the user on the catheter tube in the axial direction of the catheter. This force allows the portion of the catheter tube in its primary position to be pushed through the fold and everted into the everted position. Second, there are counter-forces acting against the force applied by the user. Among the counter-forces, the following forces should be considered. There is a friction between the outer surface of the portion of the tube in its primary position and the inner surface of the portion of the tube in everted position. The friction is primarily caused by a radially acting force created upon everting of the portion of the tube from its primary position into the everted position. Further, upon the deformation of the material during the everting of the tube, there is material resistance against the deformation. Furthermore, the body cavity is primarily closed, or it has a much smaller opening than the actual diameter of the catheter, respectively. When the catheter is inserted, the walls of the cavity are pushed from their natural position by the everting fold. Thus, forces arising from the pressure of the body tissue of the body cavity also need to be overcome. Finally, a pressure inside the cavity, including the curvatures of the cavity may play a role as well. In the end, the above-mentioned forces contribute to the increase of the friction between the outer surface of the portion of the tube in its primary position and the inner surface of the everted portion of the tube.

The basic condition to be fulfilled to make the above-described construction work is that the final counter-force acting against the force applied by the user must be smaller than the force applied by the user. During the catheterization, as the portion of the tube in its primary position is pushed towards the fold, and a portion of the tube is everted into the everted position, the counter-forces acting against the force applied by the user increase with increasing length of the portion of the tube in the everted position. At some point, the force applied by the user and the counter-force are balanced, and further everting of the catheter tube is no longer possible. In the constructions known so far (e.g. U.S. Pat. No. 4,871,358), the length of the everted portion does not exceed a few centimeters (1-2 cm), irrespective of the diameter of the catheter, material or usage of a lubrication layer, before the tube starts to collapse or bend under the axial force, the resistance of the fold, and of the friction between the everted portion and the underlying portion of the tube, which is in the primary position. As a result, there is no possibility to use such a catheter in real life, which is also a reason, why none of existing solutions has ever been industrially manufactured and marketed. Examples of similar technical solutions may be found e.g. in U.S. Pat. Nos. 3,908,635, 5,902,286, or US 2002/0133127.

DISCLOSURE OF THE INVENTION

The present invention relates to a catheter, which comprises a catheter tube everting inside-out during the process of catheterization. The presented invention overcomes the drawback of the prior art solutions by providing axial reinforcement of the tube by means of longitudinal protrusions, and by providing dilating means that dilate the circumference of the catheter tube in the everted region, while allowing for maintaining a smaller diameter in the portion of the tube which is in the primary position.

A catheter of this invention has a tube having two opposite open ends—a first end and a second end, a plurality of longitudinal protrusions extending from the first end through at least a portion of the tube and facing radially inwards, and means for dilating a circumference of the tube upon everting of the first end of the tube.

During the catheterization process, the catheter tube is everted inside-out gradually, starting from the first end. The everting forms a fold which divides the tube into two portions—a non-everted portion which is also referred herein as "primary position" of the tube, and an everted portion which is also referred herein as "everted position" or "everted region". The everted portion of the tube is folded back over the non-everted portion. The longitudinal protrusions in the non-everted portion face radially inwards, and, in the everted portion, the longitudinal protrusions face radially outwards. The everted region thus may be considered as an outer portion of the catheter tube. The portion of the tube, which is in its primary position, may thus be considered as an inner portion of the catheter tube. The portion of the tube in its primary position is slidably moveable into and out of said everted region in an axial direction, thereby changing the relative length of the portion of the tube in its primary position and the length of the everted region and the position of the fold. During the catheterization process, force is applied by the user onto the portion of the catheter tube, which is in its primary position. The force is applied in the axial direction towards the fold. This force is then axially transmitted to the fold through the portion of the catheter tube in the primary position and results in the radially outward force, which when of sufficient magnitude, transforms a portion of the tube from its primary position into its everted position and shifts the position of the fold on the tube. Thus, the everted region is lengthened, the catheter tube in its primary position is shortened and the position of the fold shifts further into the cavity, into which the catheter is being inserted. As a result, there is no friction between the surface of the catheter tube and the body tissue, because the surface of the tube, which comes into contact with the body tissue, remains stationary relative to that tissue during catheterization. Thus, the irritation of the body tissue, and the resulting pain, is minimized or eliminated at all. As the surface of the catheter tube, which comes into contact with the body tissue, is hidden from manipulation in the interior of the tube before usage, the risks of introducing infection into the body decrease. Moreover, as the catheter is not pushed through the cavity channel (no friction between the catheter tube surface and the body tissue), the bacteria residing the walls of the cavity cannot be dragged deeper into the cavity. Instead, they remain on the walls.

The drawback of the prior art solutions is the impossibility to proceed with the everting for more than a few centimeters before the tube starts to collapse and bend under the axial force and the resistance of the fold and of the friction between the everted portion and the underlying portion of the tube which is in the primary position. This invention overcomes the drawback by providing axial reinforcement of the tube by means of longitudinal protrusions, and by providing dilating means that dilate the circumference of the catheter tube in the everted region, while allowing for maintaining a smaller diameter in the portion of the tube which is in the primary position.

Before the catheterization, the whole catheter tube may be provided in its primary position, in which the longitudinal protrusions are positioned radially inwards. Alternatively, a portion of the tube at the first end of the catheter tube may be pre-folded or pre-everted inside-out, respectively, i.e. everted from its primary position with the longitudinal protrusions positioned radially inwards to its everted position, in which longitudinal protrusions are positioned radially outwards. The provision of this pre-folded portion facilitates the start of the catheterization, there is no need for the medical personnel to deal with the initiation of everting and consequently the safety of the procedure is increased and the hygiene risks are decreased.

The catheter may further comprise a guard that may be located on the pre-everted region to keep the everted region stable and fixed in a position; and/or a gripper that may be positioned on the catheter tube, that may be movable between the everted first end and the second end of the tube and allows for comfortable and smoother pushing of the catheter tube; and/or a connector that may be attached to the tube at the second end of the tube, providing an inflow/outflow connection with a collection bag or with any other medical equipment suitable for the intended use of the catheter.

In a preferred embodiment, the catheter may comprise a gripper, connected with the guard, thus providing a guiding channel for the catheter tube, thus providing for comfortable and smoother pushing of the tube, and for reducing, or even avoiding, the unwanted bending of the tube. The gripper may be equipped with means for moving along the guiding channel and for pushing or pulling the catheter tube. Thus, by pushing or pulling the gripper along the guiding channel, the catheter tube is pushed or pulled in the desired axial direction. The above-mentioned mechanism allows the catheter to be inserted into body cavity as well as to be pull out of the body cavity without irritating or traumatizing the body tissue inside the cavity.

The catheter tube comprises a plurality of longitudinal protrusions. The longitudinal protrusions may be parallel to the longitudinal axis of the tube or they may be inclined with respect to the longitudinal axis, forming a spiral. A spiral shall be understood as a three-dimensional curve that turns around the longitudinal axis of the tube, the diameter of the spiral remaining constant. The inclination angle of the longitudinal protrusions vis-a-vis the longitudinal axis of the catheter tube may range from 0 degrees for parallel protrusions up to 45 degrees, preferably 0 degrees to 30 degrees, more preferably 0 degrees to 20 degrees, even more preferably 5 degrees to 15 degrees, and even more preferably 5 degrees to 10 degrees.

The longitudinal protrusions provide an axial reinforcement of the tube, i.e. a stabilization of the tube in the axial direction, thus preventing the catheter tube from bending under the axial force exerted by the user during the process of catheterization. Moreover, the spiral structure of the protrusions allows reducing stresses arising at the fold of the catheter tube, especially when passing through curved trajectories.

The longitudinal protrusions extend from the first end of the tube through at least a portion of the catheter tube. The length of the portion of the tube comprising the longitudinal protrusions may extend through the full length of the catheter tube, it may extend to the half of the length of the catheter tube, or it may extend to any length, which may be at least 1 cm, or at least 2 cm, or at least 3 cm, or at least 4 cm, or at least 5 cm, or at least 6 cm, or at least 7 cm, or at least 8 cm, or at least 9 cm, or at least 10 cm.

The primary outer surface, which is the outer surface of the portion of the catheter tube which is in the primary position, may also have a structure. Preferably, the structure may have a form of protrusions extending in the longitudinal direction—tips. The tips may be narrower and smaller than the longitudinal protrusions and the may be of the same length as the longitudinal protrusions.

The catheter tube may be formed of one or more tubular elements, preferably of one or two tubular elements. The tubular elements may be attached to one another by any means suitable for medical instruments, e.g. by adhesive means or by welding. A combination of tubular elements provides for more design freedom in respect of materials, which may be used to manufacture the tube. In general, the first tubular element containing the first end, which is the tubular element to be everted, should be more flexible (though still stiff enough not to collapse) than the second or further tubular elements, onto which the axial force will be applied by the user during the everting. Thus, the second and further tubular elements should preferably be stiffer than the first tubular element to prevent their bending and to provide a smoother application of the catheter. The first tubular element needs to contain longitudinal protrusions, as it needs to combine sufficient flexibility for everting with sufficient axial strength (due to the longitudinal protrusions) in order to not bend under the axial force exerted by the user. Therefore, the length of the first tubular element corresponds to the length of the protrusions, which may be at least 1 cm, or at least 2 cm, or at least 3 cm, or at least 4 cm, or at least 5 cm, or at least 6 cm, or at least 7 cm, or at least 8 cm, or at least 9 cm, or at least 10 cm. The second and further tubular elements are not everted, they form the part of the tube which remains in its primary position during the catheterization process, and thus they can be made of a material stiff enough to resist to the axial force exerted by the user without the need for the presence of the longitudinal protrusions.

When the tube is made of one tubular element, often the longitudinal protrusions will be present over the whole length of the tube. In any case, the longitudinal protrusions need to be present in at least a portion of the length of the catheter tube, starting from the first end of the tube. The remaining portion of the tube may comprise longitudinal protrusions and/or other means for increasing the stiffness and resistance to the axial force exerted by the user—such as an increased thickness of the wall of the tube or a layer of a material, which is stiffer than the material of the tube.

In a preferred embodiment, the tube may be provided with the longitudinal protrusions over the whole length of the tube. Subsequently, the non-everting portion of the tube undergoes a heat treatment, such that the longitudinal protrusions are "welded" together to form the stiffened part of tube. Advantageously, due to the heat treatment, the tube is stiffer in comparison to other stiffening methods.

The everting of the catheter tube inside-out is possible only if the final force acting against the force applied by the user is smaller than the force applied by the user. This is the basic condition to be fulfilled in order to successfully apply the catheter. The counter-force acting against the force applied by the user is primarily determined by the radially acting force created upon everting of the tube, the material resistance against the material deformation arising at the fold, and by the friction arising between the touching surfaces—the outer surface of the tube in its primary position and the inner surface of the everted region, and increases with the increasing length of the everted region. In order to evert the tube without creating the counter-forces that would be too large to overcome, it is necessary to increase the diameter—and so the circumference—of the tube upon everting. Therefore, dilating means must be present at least in the portion of the tube, which is to be everted, i.e., in a portion of the length of at least 1 cm, or at least 2 cm, or at least 3 cm, or at least 4 cm, or at least 5 cm, or at least 6 cm, or at least 7 cm, or at least 8 cm, or at least 9 cm, or at least 10 cm, always extending from the first end of the tube. In the present invention, several examples are provided of suitable dilating means which allow the catheter tube to dilate its diameter upon everting. The dilating means may consist in various configurations of the longitudinal protrusions, such as unevenly distributed protrusions and/or dilatable protrusions, and/or a layer of flexible material forming the tube and supporting the longitudinal protrusion.

The unevenly distributed protrusions allow the diameter of the tube in its primary position to be reduced by deforming its otherwise spherical circumference. Upon everting, the deformation ceases to exist and the tube may be fully stretched out in its circumference, thereby dilating it. The dilatable protrusions have dilatable frames, which may be stretched out upon everting of the catheter tube, thus allowing the catheter tube to be fully stretched out in its circumference, thereby dilating it. The layer of flexible material allows the dilatation of the diameter of the catheter tube upon everting; therefore, the term "flexible" should be understood as flexible and extensible.

The friction between the two touching surfaces may further be reduced by application of a lubrication coating, or by the tips of the primary outer surface. The tips may be provided on the primary outer surface and the everted inner surface, thus crossing each other, which reduces the contact area of the two surfaces and so the friction between the two surfaces, allowing for a smoother sliding.

These dilating means may be provided separately or in combinations.

In a preferred embodiment, the longitudinal protrusions and dilatable protrusions may be alternating along the circumference of the tube, such that a dilatable protrusion is always positioned between two adjacent longitudinal protrusions. The even distribution of dilating protrusions provides the dilatation of the circumference of the catheter tube upon everting, as well as reduction of the deformation of the circular shape of the tube and of the free passage channel.

In further preferred embodiment, the longitudinal protrusions of any of the above-mentioned configurations may be provided in a "shutter" structure, such that the longitudinal protrusions are folded or inclined with respect to their normal.

In another preferred embodiment, the dilating means of any of the above-mentioned configurations may also be provided in combination with a tapered shape of the tube.

The tapered shape of the catheter tube is provided by continuous change of the diameter of the tube (both the inner diameter and the outer diameter) such that the diameter of the first end of the catheter tube—the end to be everted—is larger than the diameter of the second end of the catheter tube and so the everted portion of the tube has larger diameter than the on-everted portion. Thus, while the force is applied onto the non-everted portion in the axial direction, and the everted portion is being folded back over the non-everted portion, the difference of diameters is continuously increasing, thereby further reducing the friction between the outer surface of the tube in its primary position and the inner surface of the everted region. The difference of the diameters may range from 0.1 mm up to 3 mm, preferably it may range from 0.1 mm up to 2 mm, more preferably from 0.1 mm to 1 mm, more preferably from 0.2 mm to 1 mm, more preferably from 0.3 mm to 1 mm, even more preferably from 0.4 mm to 1 mm and even more preferably from 0.5 mm to 1 mm. This difference is independent of the length of the catheter tube, e.g. the difference of 1 mm may apply to any length catheter tube.

In another preferred embodiment, the longitudinal protrusions may be pre-formed during manufacture of the catheter tube and expanded upon everting the catheter tube inside-out.

The pre-formation of the longitudinal protrusions may be provided by radially cutting or perforating the catheter tube between the primary inner surface and the primary outer surface of the tube, such that the perforations extend from the primary inner surface of the catheter tube towards the primary outer surface and/or from the primary outer surface of the catheter tube towards the primary inner surface of the tube, depending on whether protrusions or dilatable protrusions are to be provided. In the case of longitudinal protrusions, the primary outer surface shall not be perforated in order to provide the movable connection joints between adjacent protrusions. In the case of dilatable protrusions, the primary inner surface shall not be perforated in order to provide the dilatable frames of the dilatable protrusions.

The perforations extend from the first end of the tube through at least part of the catheter tube in its longitudinal direction. In a preferred embodiment, the length of perforations corresponds to at least the part of the tube that is to be everted.

The perforations are provided at several places on the circumference of the catheter tube, the distance between the perforations determining the width of the longitudinal protrusion and the number of the perforations determining the number of longitudinal protrusions. The number of perforations corresponds to the number of protrusions, i.e. four perforations shall be provided for four longitudinal protrusions, twelve perforations shall be provided for twelve longitudinal protrusions, etc.

The perforations allow pre-forming of the longitudinal protrusions. When the catheter is to be used, and the first end of the catheter tube is everted, the perforations tear up under the tension acting at the fold of the tube upon everting and the longitudinal protrusions expand, such that the inter-protrusional space is formed between the adjacent protrusions and, in case of dilatable protrusions, the inner space embodied by the dilatable frame is created, thus dilating the circumference of the catheter tube.

Apart from the cuts or perforations, another suitable means for pre-forming the longitudinal protrusions may be provided, e.g. a modified material or different material may be provided along the portion of the tube, where the movable contact joints are to be formed, where the modified or different material has properties, which allow the material to tear up in a preferred direction, i.e. along the portion of the tube, where the movable contact joints are to be formed. Advantageously, different materials or various modifications of material may be applied in one step directly by the manufacture of the tube, which reduces the complexity of the manufacture.

In a preferred embodiment, the protrusions inclined with respect to the longitudinal axis of the catheter tube may be pre-formed in a way similar to the way described above, preferably by providing cuts or perforations inclined with respect to the longitudinal axis of the catheter tube.

In a preferred embodiment, the perforations or cuts may be provided discontinuously, in a structure, such that the expanded longitudinal protrusions are deformed in comparison to their straight elongated shape created by continuous perforations. As the perforations are provided discontinuously in this embodiment, the inter-protrusional spaces formed from the perforations are embodied by the protrusions, thereby deforming their straight elongated shape.

In this embodiment, the cuts or perforations are provided over the whole thickness of the tube in order to ensure full dilatation of the inter-protrusional spaces. In order to cover the created inter-protrusional spaces, thus ensuring the sterility of the interior of the catheter tube, a layer of flexible material is provided on the primary outer surface of the catheter tube.

The width and the actual shape of the protrusions may be varied by varying the density, size and the distribution of the cuts or perforations. The perforations may be positioned regularly, such that the perforated portions and the non-perforated portions are alternating in all directions, so that each perforation is positioned between two non-perforated portions in both the longitudinal and the transversal direction. The transversally adjacent perforations may overlap in the longitudinal direction over less than one half of the length of the perforation, preferably over less than one third of the length of the perforation or over less than one fourth of the length of the perforation. This mutual shift in perforations, and so the shift in the inter-protrusional spaces provides a structure of the secondary inner surface, which may help to further decrease the friction between the two surfaces upon everting, allowing a smoother sliding.

Thus, the discontinuous cuts or perforations allow pre-forming of the longitudinal protrusions. When the catheter is to be used, and the first end of the catheter tube is everted, the cuts or perforations tear up under the tension acting at the fold of the tube upon everting, the inter-protrusional spaces are formed, and the circumference of the catheter tube is dilated by dilating the created inter-protrusional spaces.

The materials used for manufacture of individual components of the catheter include silicon, thermoplastic elastomers (TPE), or thermoplastic polyurethane (TPU). The materials must be suitable for medical instruments, thus being of a medical grade quality. The materials should preferably have a hardness is the range of Shore A 50 to Shore A 90, depending on the component.

In a preferred embodiment, the dilating means of any of the above-mentioned configurations may also be provided in combination with the application of an active material and/or with application of different materials for different parts of the tube.

The active material allows altering its shape in a controllable manner, i.e. usually in reaction to changes in external conditions, such as pressure, temperature, pH, etc., while this kind of change may or may not be reversible.

In a preferred embodiment, the active material may recognize the tension at the fold upon everting the portion of the catheter tube, or it may recognize changes in temperature or pH of the environment. In reaction to such a change of external conditions, it may change its structure, e.g. by tearing apart the material bonds, such that a dilated circumference of the catheter tube upon everting is provided. The other properties of the material, such as elasticity or strength may or may not remain unchanged. It is preferred that the material loses its properties upon everting, e.g. when the elasticity of the material is lost, the friction between the inner surface of the everted region and the outer surface of the non-everted portion and so the overall counterforce is reduced. The person skilled in the field of materials is aware of the properties and types of active materials and would be able to select a suitable active material based on his knowledge.

In a preferred embodiment, the active material may also be provided in combination with other material or materials in order to reduce the manufacture costs. For example, a first, stiffer, material may be used for the longitudinal protrusions, while an active material is used for the movable contact joints between the adjacent protrusions. Alternatively, catheter tube may be made of a material that can be modified for the manufacture of the movable contact joints between the adjacent protrusions, e.g. by some suitable additives, in such a way that the longitudinal protrusions are stiffer than the movable contact joints between the adjacent protrusions. The desired properties may even be achieved by providing one single material, adjusting its properties in one step directly by the manufacture, e.g. by varying thickness of the tube. Different materials or various modifications of material may also be applied in one step directly by the manufacture of the tube. This simpler and cheaper manufacture reduces the number of components to be assembled and requires less manipulation with the tube, thereby reducing number of defective pieces as well as potential failures during application.

A catheter tube of the invention may be extruded, injection molded or 3D printed—directly so that the longitudinal protrusions face radially inwards. As an alternative to the injection molding, the catheter tube may also be dip molded or vacuum formed. The person skilled in the field of medical instruments and their manufacture is aware of the aforementioned and other available manufacture methods and would be able to select a method suitable for manufacture of a particular catheter type.

Alternatively, the catheter tube may be produced so that in a first step, it is extruded in a position "inside-out", i.e., so that the longitudinal protrusions face radially outwards, and in a second step, the extruded tube is everted in its full length so that the longitudinal protrusions face radially inwards. Following these two manufacture steps, the stresses arising at the fold upon everting of the tube are reduced, because during the catheterization process the tube is in fact everted back into its natural position. In one preferred embodiment, in the second step, the extruded tube is everted in part of its length (in majority of its length, preferably in at least 90% of its length), but a portion of the tube is left in the position where the longitudinal protrusions face radially outwards—thereby forming a pre-folded region at the first end of the tube.

The method of manufacture providing the longitudinal protrusions radially inwards is especially advantageous for the catheter tube made of active material or in a combination with the active material, because in this embodiment, the main advantage of the double everted catheter tube, i.e. the reduction of stresses arising at the fold upon everting of the tube because of everting the tube back into its natural position, is achieved by the active material.

In the preferred embodiment with the shutter structure, the inclined longitudinal protrusions may be manufactured in the same way as the non-inclined longitudinal protrusions, or, alternatively, the catheter tube may initially be manufactured as a smooth tube and the protrusions may be subsequently provided by folding the tube along its circumference. The folded protrusions may extend over the whole length of the tube, or they may extend from the first end of the catheter tube through at least a portion of the catheter tube, which is to be everted—which is especially advantageous in combination with a tapered shape of the tube.

DETAILED DESCRIPTION OF THE INVENTION

Figure 1:
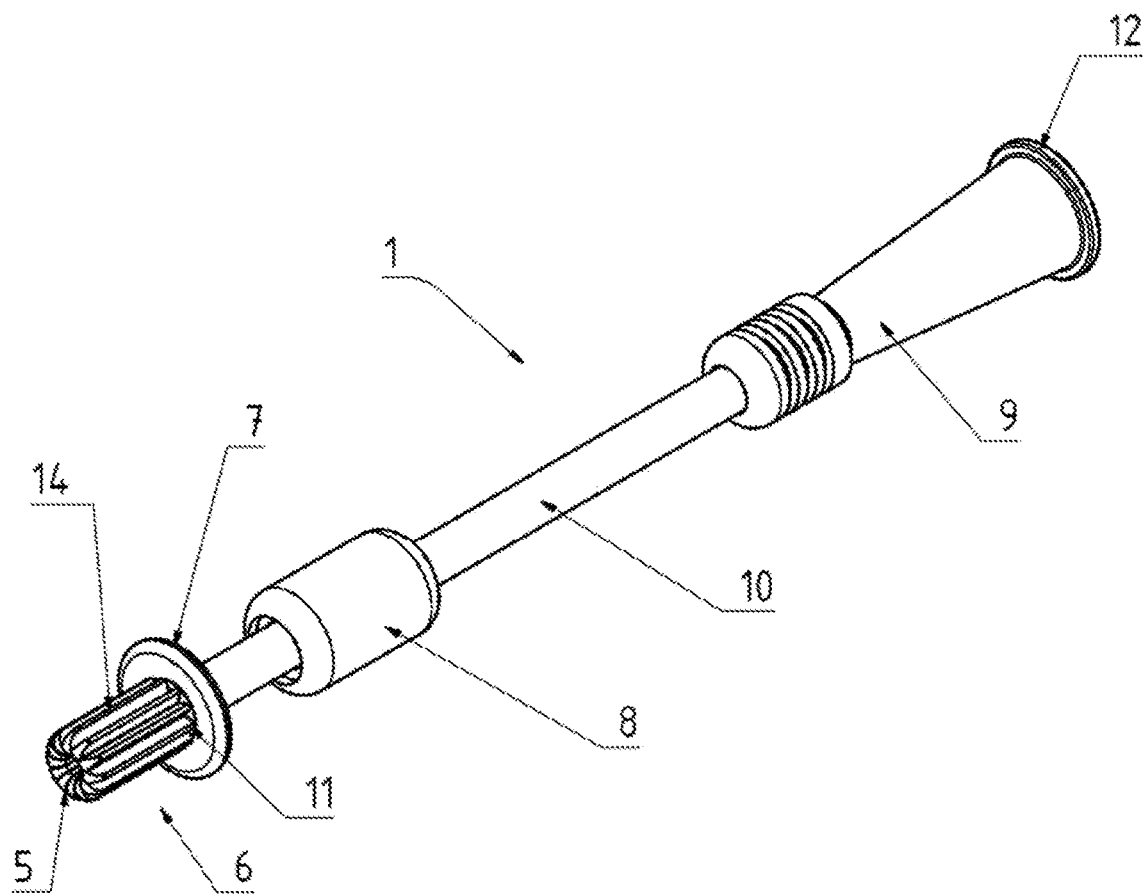
FIG. 1 shows a perspective view of a catheter of one of the preferred embodiments.
Figure 2:
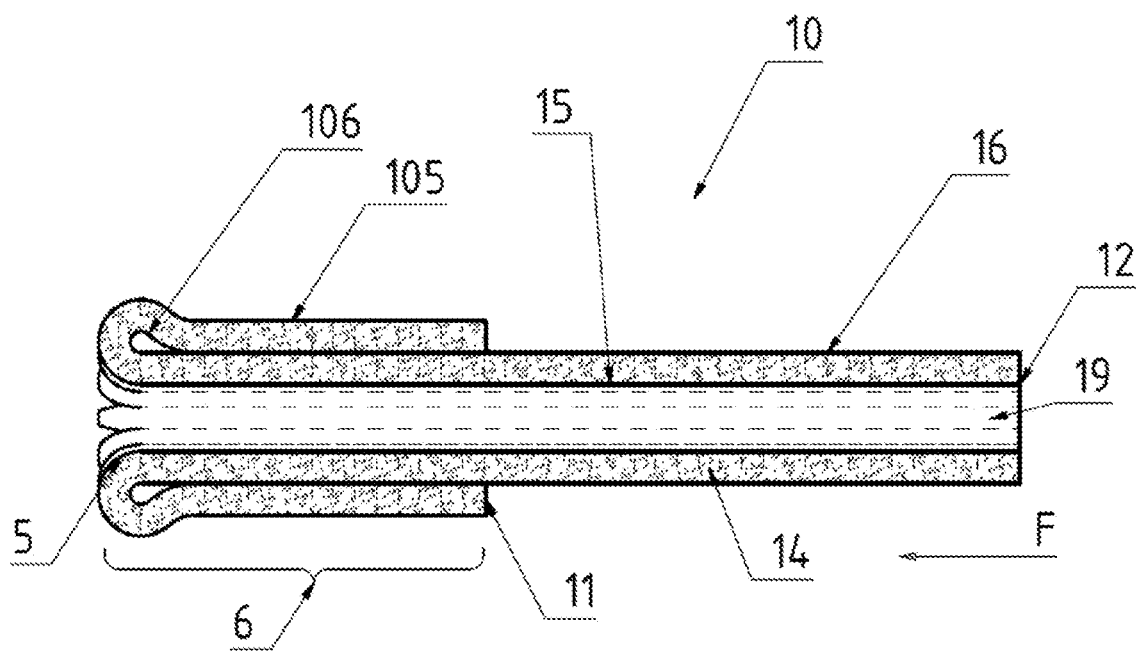
FIG. 2 shows a longitudinal cross-section of the catheter tube. Both, a portion of the tube in its primary position and a portion of the tube in the everted position can be seen, showing a structure of a fold, contact of the primary outer surface and the everted inner surface, and a direction, in which a force is applied by the user.

Referring to FIG. 1, which shows one possible embodiment of the catheter of this invention, the catheter 1 of the invention comprises a tube 10 having two opposite open ends—a first end 11 and a second end 12, and a plurality of longitudinal protrusions 14. The first end 11 corresponds to the end of the tube 10, which is proximate to the body cavity, into which the catheter is being inserted. The second end 12 corresponds to the end, which is distant from the body cavity and stays external during the catheterization. The catheter tube 10 is gradually everted inside-out from the first end 11 i.e. everted from its primary position with the longitudinal protrusions 14 positioned radially inwards to its everted position, in which longitudinal protrusions 14 are positioned radially outwards. Upon everting, a fold 5 and an everted portion 6 are created. A guard 7 may be attached to the catheter tube 10, being located on the everted portion 6. Further, the catheter 1 may comprise a gripper 8, the gripper 8 being positioned on the catheter tube 10 and movable between the everted first end 11 and the second end 12 of the tube 10. The gripper 8 may surround the tube 10 and may have a frame of substantially cylindrical shape. Finally, a connector 9 may be attached to the tube 10 at the second end 12 of the catheter tube 10.

In the following, individual components of the catheter will be described in more detail with reference to the attached figures. The figures are merely illustrative, and individual components can be used separately, not necessarily in the combination with the specific embodiments of other components as depicted in the figures.

Figure 3:
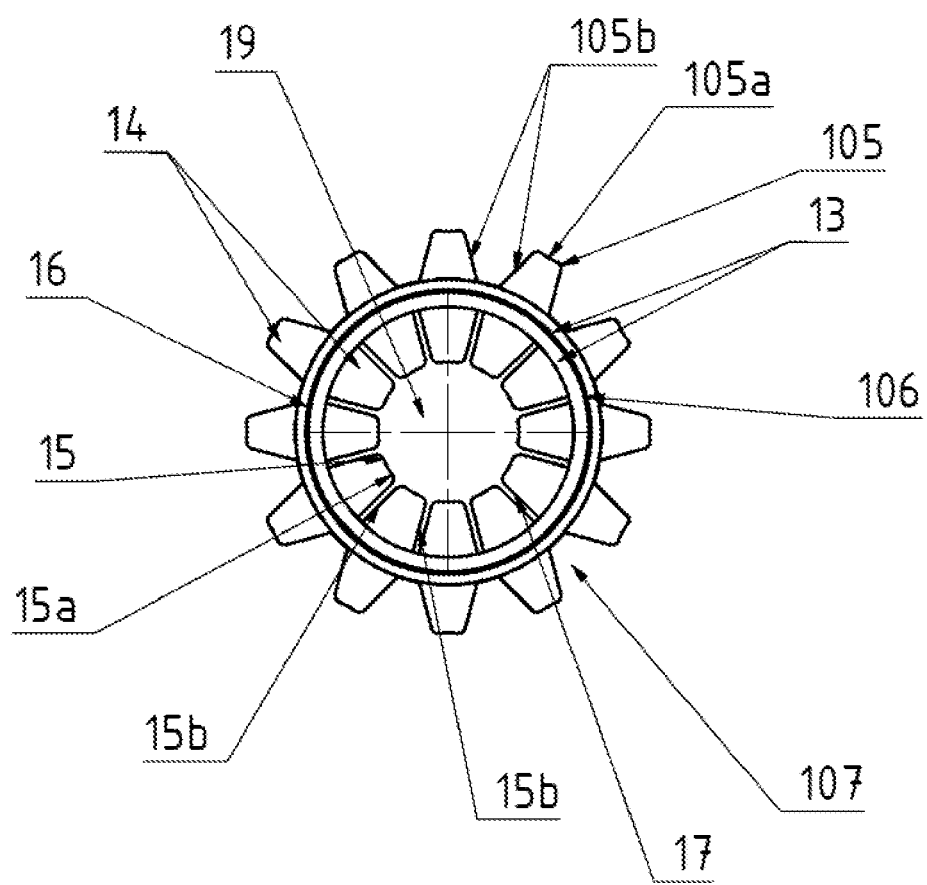
FIG. 3 shows a transversal cross-section of the catheter tube. Both, a portion of the tube in its primary position and a portion of the tube in the everted position can be seen, in a configuration with longitudinal protrusions distributed around the whole circumference of the catheter tube and a layer of flexible material according to a preferred embodiment.

The catheter tube 10 may be formed by longitudinal protrusions 14 or it may be formed by longitudinal protrusions 14 and a layer of flexible material 13 (as shown in FIG. 3).

The longitudinal protrusions 14 extend from the first end 11 of the tube 10. The length of the longitudinal protrusions 14 may extend through at least the part of the tube 10 that is to be everted. It may extend through the full length of the catheter tube 10, i.e. between the first end 11 and the second end 12 of the tube 10, it may extend from the first end 11 of the tube 10 to the half of the length of the catheter tube 10, or it may extend from the first end of the tube 10 to any length of at least 1 cm, or at least 2 cm, or at least 3 cm, or at least 4 cm, or at least 5 cm, or at least 6 cm, or at least 7 cm, or at least 8 cm, or at least 9 cm, or at least 10 cm. Optionally, the longitudinal protrusions 14 may extend through the full length of the tube 10, but may be stuck or glued together along the portion of the tube comprising the second (distal) end 12 of the tube 10, which is not everted, in order to increase the stiffness of that portion of the tube 10.

The flexible layer 13 may extend from the first end 11 of the tube and may cover at least the portion of the tube 10 that is to be everted; i.e. the portion of the tube 10 being covered with the flexible layer 13 and the portion of the tube 10 comprising longitudinal protrusions 14 may have the same lengths. The flexible layer 13 may, however, cover the full length of the catheter tube 10, it may cover the half of the length of the catheter tube 10, or it may cover any length of at least 1 cm, or at least 2 cm, or at least 3 cm, or at least 4 cm, or at least 5 cm, or at least 6 cm, or at least 7 cm, or at least 8 cm, or at least 9 cm, or at least 10 cm, always extending from the first end 11 of the tube 10. The flexible layer 13 allows the dilatation of the diameters $D1_{in}$, $D1_{out}$ (diameters are described below, see FIG. 4) of the tube 10 upon everting; therefore, the term "flexible" should be understood as flexible and extensible. The flexible layer 13 may be made of any material of suitable hardness and suitable for medical instruments, e.g. of thermoplastic polyurethane (TPU) of hardness Shore A ranging between 50 and 80. By the way of example, Tecoflex™ can be used, having a Shore A 72 hardness. The longitudinal protrusions 14 may be made of any material of suitable hardness and suitable for medical instruments, the material being generally harder than the material of the flexible layer 13, e.g. of thermoplastic polyurethane (TPU) of Shore A hardness ranging between 60 and 90. By the way of example, Estane can used, having a Shore A 87 hardness. The longitudinal protrusions 14 and the flexible layer 13 may be fastened together by any means known in the art, suitable for medical instruments. Preferably, the protrusions 14 and the flexible layer 13 are fastened together during the manufacture, e.g. by multilayer extrusion, co-extrusion, etc.

Further referring to FIG. 3, in the primary position of the tube 10, the tube 10 has a primary inner surface 15 and a primary outer surface 16. The primary inner surface 15 is formed by top surfaces 15a and side surfaces 15b of individual longitudinal protrusions 14. The primary outer surface 16 may be formed by the primary outer surface of the longitudinal protrusions 14 or it may be formed by a layer of flexible material 13, on which the longitudinal protrusions 14 are disposed. The adjacent side surfaces 15b of the two adjacent protrusions 14 form an inter-protrusional space 17. The two adjacent protrusions 14 may be separated or connected by a movable contact joint 18 (can be seen e.g. in FIG. 4 or 8) at the primary outer surface 16. The inner primary surface 15 forms the free passage channel 19 with the diameter $D1_{in}$. The diameter $D1_{in}$ of the free passage channel 19 may be larger in the part of the tube 10, which comprises the second end 12, if that part does not comprise protrusions.

Still referring to FIG. 3, in the secondary position of the tube 10, the primary inner surface 15, formed by top surfaces 15a and side surfaces 15b of individual longitudinal protrusions 14, becomes an everted outer surface 105 and the primary outer surface 16 becomes an everted inner surface 106. The everted outer surface 105 is formed by top surfaces 105a and side surfaces 105b of individual longitudinal protrusions 14. The top surfaces 105a of the individual longitudinal protrusions provide the contact surfaces with the body tissue of the cavity (not shown), into which the catheter tube 10 is inserted. The adjacent side surfaces 105b of the two adjacent protrusions 14 form an inter-protrusional space 107, which is wider than the inter-protrusional space 17 in the primary position. The two adjacent protrusions 14 may be separated or connected by a movable contact joint 108 at the secondary inner surface 106. The movable contact joint 18, 108 allows the longitudinal protrusions 14 to be "opened" from the primary position to the everted position, by providing the inter-protrusional space 107 wider than the inter-protrusional space 17. Thus, the longitudinal protrusions 14 not only provide the axial reinforcement to the catheter tube 10; they also provide a support for the walls of the body cavity and clear the passage for the catheter tube 10 by gently pushing the walls of the body cavity aside.

The primary outer surface 16—and the everted inner surface 106—may also have a structure. The structure may be provided intentionally during the manufacture. Preferably, the structure may have a form of protrusions extending in the longitudinal direction—tips 20. The tips may be narrower and smaller than the longitudinal protrusions and the may be of the same length as the longitudinal protrusions. The tips may be provided as a result of manufacturing process of the tube or of forming the longitudinal protrusions 14, or, optionally, a form or mold used for the manufacture of the catheter tube 10 may be shaped to provide the tips 20 (see e.g. FIG. 5a, 5b, 5c or 9).

Figure 10:
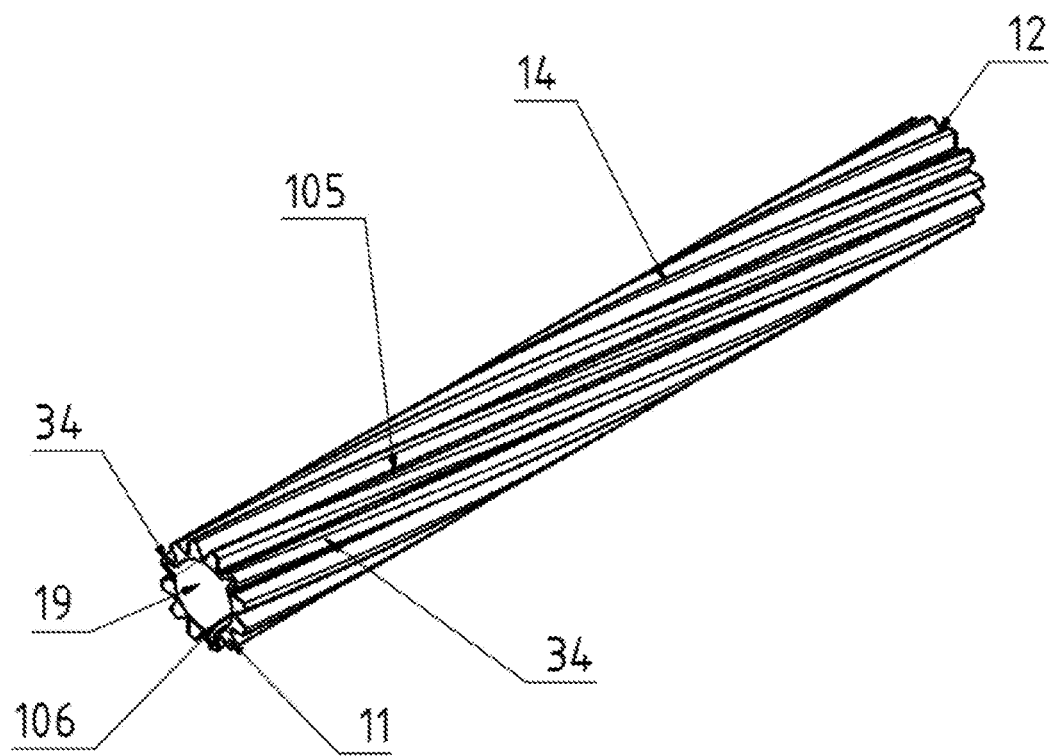
FIG. 10 shows the catheter tube in the everted position with the longitudinal protrusions forming a spiral. A configuration with dilatable protrusions according to a preferred embodiment is provided.

The longitudinal protrusions 14 may be parallel to the longitudinal axis (the axis not shown) of the tube 10, but may be also inclined with respect to the longitudinal axis of the tube 10, forming a spiral around the longitudinal axis of the tube 10, the diameter of the spiral remaining constant. An everted position of a spiral can be seen in FIG. 10. The inclination angle may range from 0 degrees (parallel protrusions) to 45 degrees. Having the spiral structure, the everted inner surface 106 of the everted portion 6 of the tube 10 cross the primary outer surface 16 of the tube 10 in the primary position. The inclination angle may preferably be large enough to provide at least one turn of the longitudinal protrusions 14, thus providing for the same length of protrusions at the fold 5, when the tube 10 passes through curved trajectories. Thus, the stresses arising at the fold 5 are balanced, i.e. equal around the whole circumference of the fold 5. Preferably, the inclination angle ranges from 0 degrees to 30 degrees, more preferably 0 degrees to 20 degrees, more preferably 5 degrees to 15 degrees, and even more preferably 5 degrees to 10 degrees.

Furthermore, when the longitudinal protrusions are inclined, the tips 20 provided on the primary outer surface 16 and everted inner surface 106 may help to decrease the friction between the two surfaces, allowing a smoother sliding. The tips 20 may follow the spiral structure of the longitudinal protrusions 14. Thus, when the everted inner surface 106 of the everted portion 6 slides along the underlying portion of the tube 10 which is in the primary position, the tips 20, forming a spiral, cross each other, thereby reducing the contact surface and so the friction between the two surfaces.

The catheter tube 10 may comprise longitudinal protrusions 14 of various shapes and sizes, for instance all of the longitudinal protrusions 14 may preferably be of the same shape and size. Around the circumference, the longitudinal protrusions 14 may be distributed next to each other, being connected or not, or they may be distributed equidistantly around the circumference of the tube 10. The longitudinal protrusions 14 may also be distributed unevenly.

The number of longitudinal protrusions 14 is not limited. Preferably, the catheter tube 10 comprises at least four longitudinal protrusions 14, more preferably, the catheter tube 10 comprises four to twelve longitudinal protrusions 14, and even more preferably, the catheter tube 10 comprises ten or twelve longitudinal protrusions 14. Depending on the shape of the protrusions, if the number of longitudinal protrusions 14 is too high, the structure created by the protrusions may vanish and the dilating properties may cease. The manufacture may also become more difficult.

The catheter tube 10 may be formed of one or more tubular elements, preferably of a first and a second tubular element (not shown). The tubular elements may be attached to one another by any means suitable for medical instruments, e.g. by adhesive means or welding. The first tubular element may comprise the first end 11 of the catheter tube 10. Preferably, the length of the first tubular element may correspond to the length of the longitudinal protrusions 14, which may be at least 1 cm, or at least 2 cm, or at least 3 cm, or at least 4 cm, or at least 5 cm, or at least 6 cm, or at least 7 cm, or at least 8 cm, or at least 9 cm, or at least 10 cm. In one preferred embodiment, the length of the first tubular element is 23 cm and the length of the corresponding second tubular element may be at least 30 cm. The diameters of the tube or tubular elements correspond to diameters of typical catheters used in the medical practice.

The catheter tube 10 may be in its primary position before the catheterization. In the primary position, the longitudinal protrusions 14 are positioned radially inwards. At the first end 11 of the catheter tube 10, the catheter tube 10 may be everted from its primary position with the longitudinal protrusions positioned radially inwards to its everted position, in which longitudinal protrusions are positioned radially outwards. Upon everting, the fold 5 and the everted portion 6 of the tube 10 are created. The length L of the everted portion 6 of the tube 10 may be defined as the length between the fold 5 and the everted first end 11 of the tube 10. The length L of the everted portion 6 increases during the catheterization, starting from the initial length L1 up to the length L2, which may be any length required for successful catheterization. However, the maximal length L2 of the everted portion 6 may be one half of the full length of the tube 10, when the everted portion 6 of the tube 10 is of the same length as the non-everted portion of the tube 10 in its primary position (there is no further space for pushing the tube 10). The length L1 of the everted part of the tube 10 may be at least 5 mm, preferably 15 mm. The first end 11 of the tube 10 may be everted by the user, providing the initial everted portion 6 of the length L1 just before the application of the catheter 1. Preferably, the first end 11 of the tube 10 may be pre-folded, or pre-everted, respectively, during the manufacture of the catheter 1. This provision facilitates the start of the catheterization, there is no need for the medical personnel to deal with the initiation of everting and consequently the safety of the procedure is increased and the contamination risks are decreased.

Figure 4:
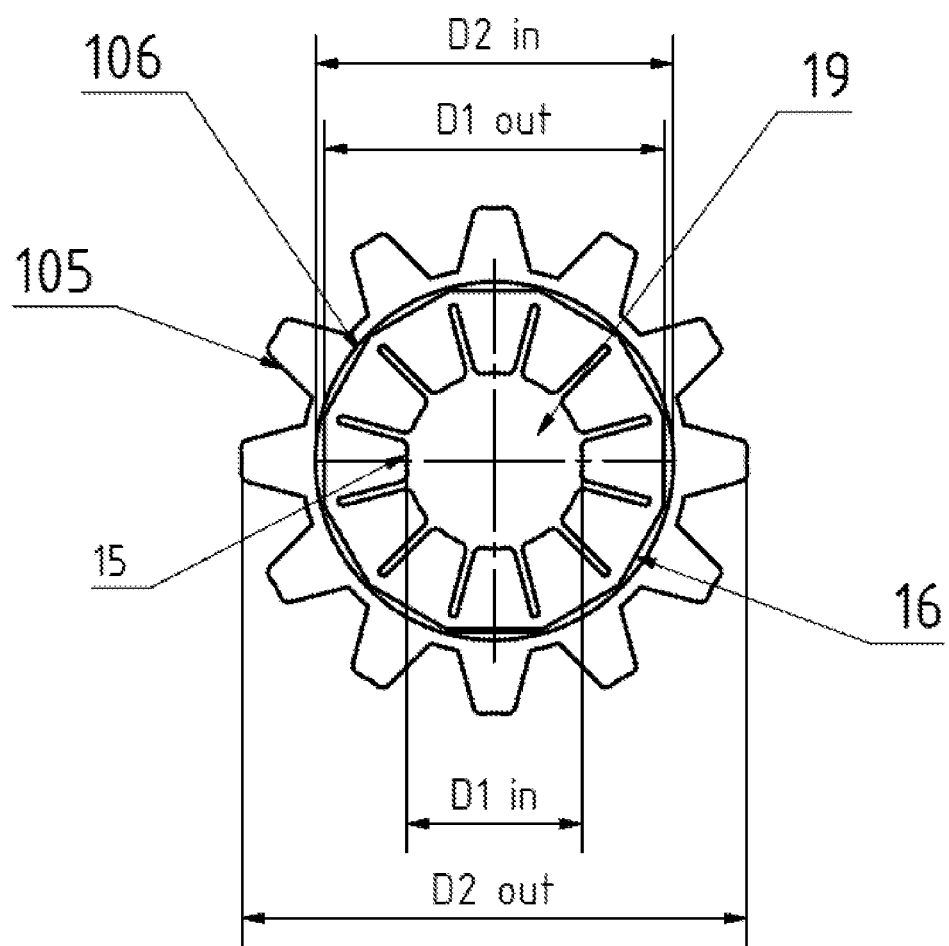
FIG. 4 shows a transversal cross-section of the catheter tube. Both, a portion of the tube in its primary position and a portion of the tube in the everted position can be seen, showing diameters determined by these positions.
Figure 5A:
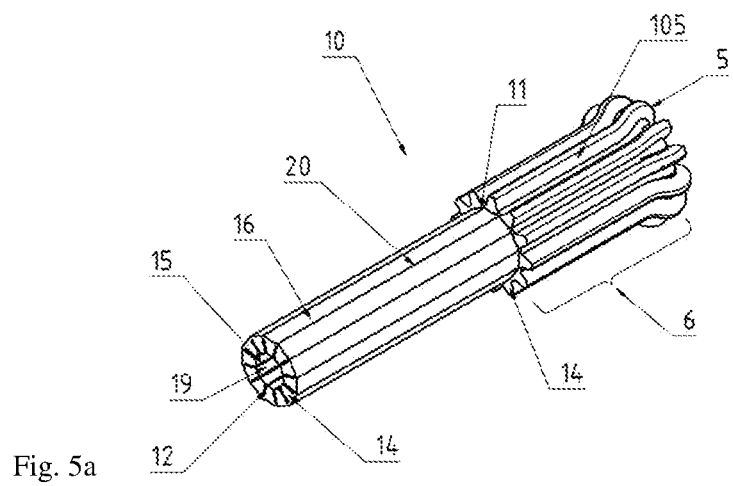
FIGS. 5a and 5b show a side perspective view of the catheter tube in a configuration with longitudinal protrusions distributed around the whole circumference of the catheter tube. Both, a portion of the tube in its primary position and a portion of the tube in the everted position can be seen.
Figure 5B:
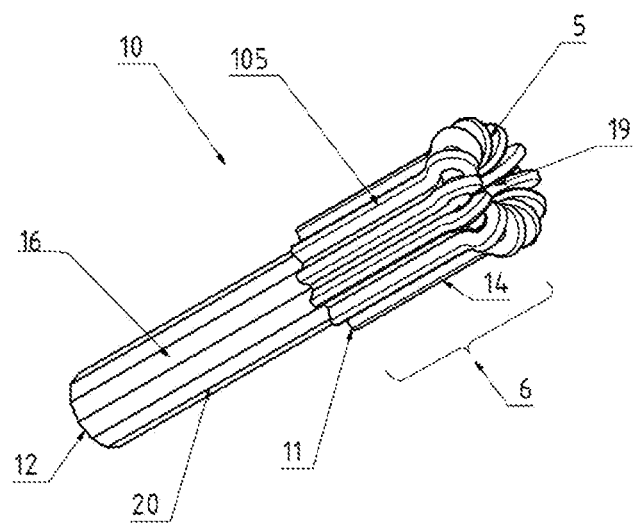
Figure 5C:
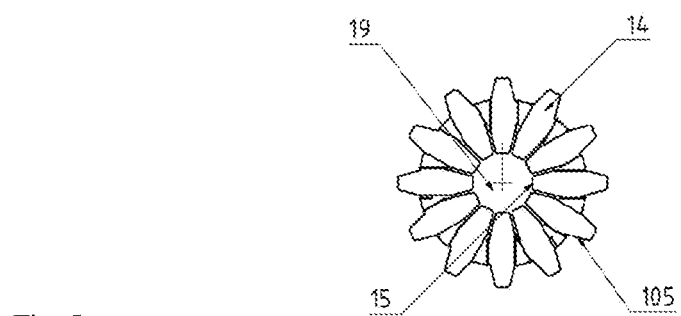
FIG. 5c shows a front view of the fold of the catheter tube.
Figure 6:
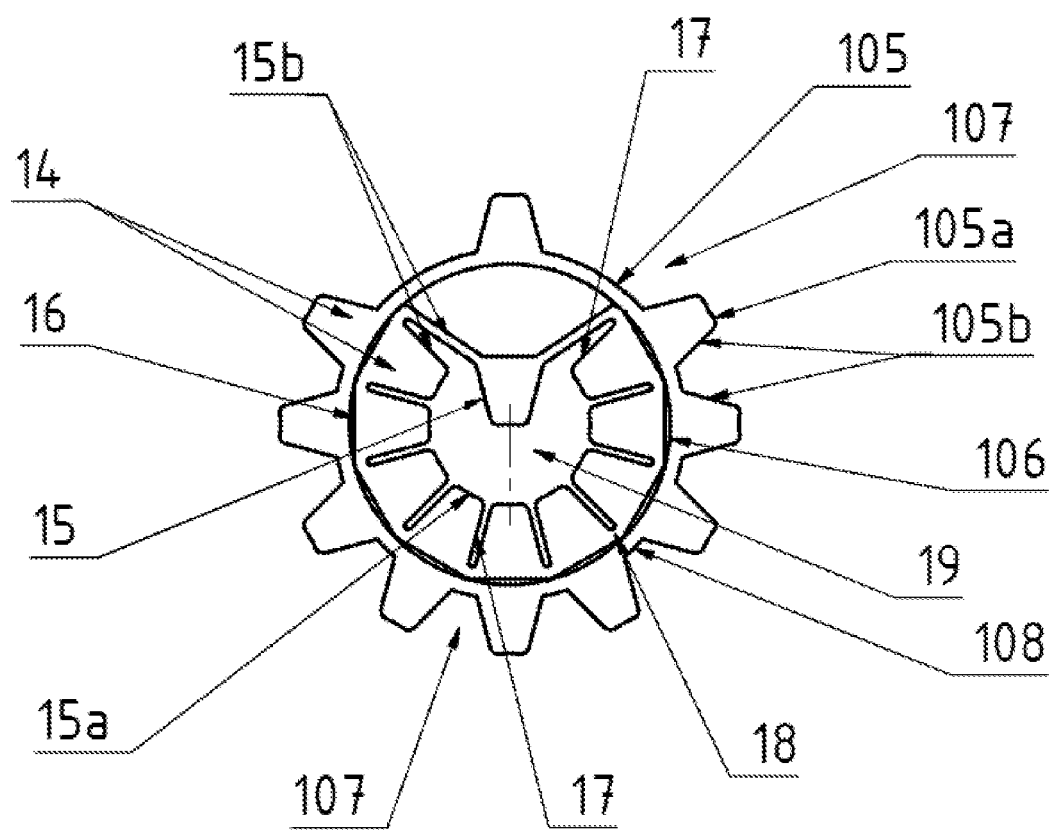
FIG. 6 shows a transversal cross-section of the catheter tube in a configuration with unevenly distributed protrusions according to a preferred embodiment. Both, a portion of the tube in its primary position and a portion of the tube in the everted position can be seen.
Figure 7A:
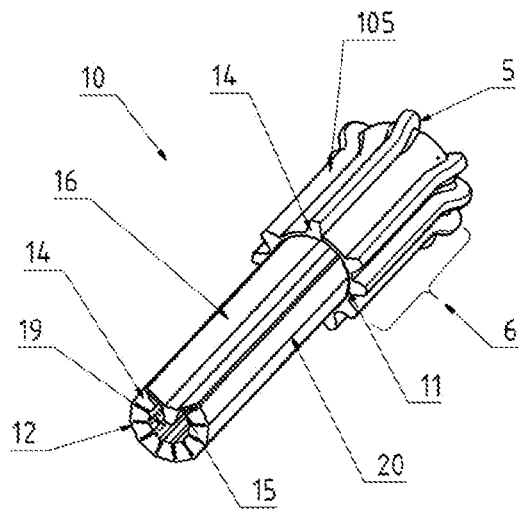
FIGS. 7a and 7b show a side perspective view of the catheter tube in a configuration with unevenly distributed protrusions. Both, a portion of the tube in its primary position and a portion of the tube in the everted position can be seen.
Figure 7B:
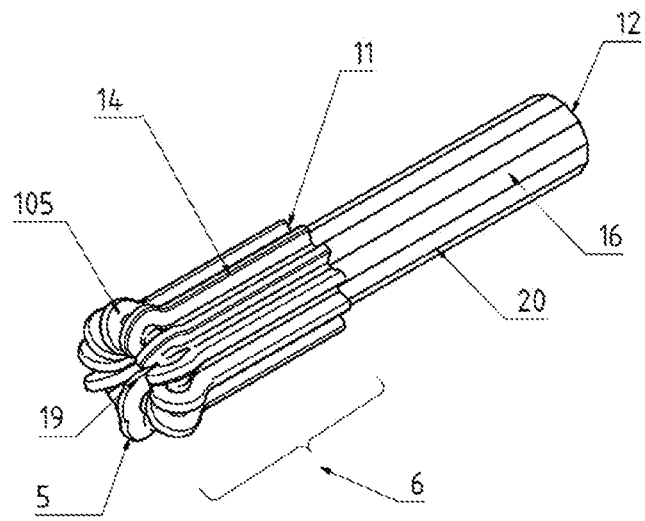
Figure 7C:
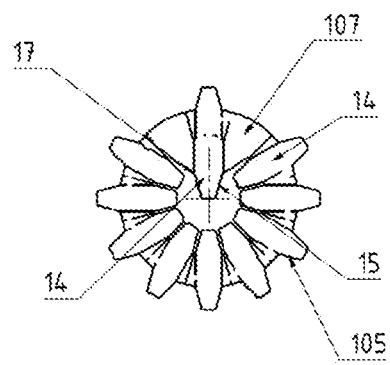
FIG. 7c shows a front view of the fold of the catheter tube.

A cross-section of the catheter tube 10 in both the primary position and the everted position is shown in FIG. 4. The primary inner surface 15 determines the primary inner diameter Din, (given by pairs of opposite protrusions). The primary outer surface 16 of the tube 10 determines the primary outer diameter $D1_{out}$ of the tube 10. In the everted position, the everted outer surface 105 of the everted portion 6 has an everted outer diameter $D2_{out}$ (again, given by pairs of opposite protrusions). The everted inner surface 106 of the everted portion 6 has an everted inner diameter $D2_{in}$. Notably, the everting of the tube 10 may be successful only if $D2_{in} > D1_{out}$ and $D2_{out} > D1_{in}$, i.e. if primary inner diameter $D1_{in}$ of the tube 10 may be enlarged to the everted outer diameter $D2_{out}$ and the primary outer diameter $D1_{out}$ of the tube 10 in its primary position may be enlarged to the everted inner diameter $D2_{in}$ of the tube 10 in its everted position.

The present invention provides the catheter, which comprises means, which allow the catheter tube 10 to dilate its diameter upon everting ($D1_{in} \rightarrow D2_{out}$, $D1_{out} \rightarrow D2_{in}$), or to dilate a circumference of an everted portion 6 of the tube 10 upon everting the tube 10 inside-out from the first end 11 vis-a-vis a circumference of a non-everted portion of the tube 10, respectively. The dilating means may consist in various configurations of the longitudinal protrusions 14, such as unevenly distributed protrusions 14 and/or dilatable protrusions 34 and/or a combination of protrusions 14, 34 with a layer of flexible material 13.

The longitudinal protrusions 14 may be distributed unevenly around the circumference of the tube 10, i.e. the longitudinal protrusions 14 cover only part of the circumference of the tube 10. One or more protrusions 14 may be missing, preferably at least two protrusions 14 may be missing. A portion of the circumference of the tube 10, with protrusions 14 may preferably be larger than a portion of the circumference of the tube 10 without protrusions. According to one embodiment, as can be seen in FIGS. 6, 7a, 7b, 7c, the arrangement of the unevenly distributed protrusions 14 may be achieved by leaving out at least one and preferably at least two of the protrusions 14. Preferably, there may be at least one longitudinal protrusion 14 left between the missing protrusions. Other distributions may be provided with various shapes and sizes of the protrusions 14 and with various widths of the inter-protrusional spaces 17 and 107.

As a result, the catheter tube 10 is intentionally allowed to collapse inwards, deforming the substantially circular opening of the free passage channel 19. This deformation allows the diameter of the tube 10 in its primary position to be reduced; the diameter (though the opening is not spherical anymore) may be less than the primary inner diameter $D1_{in}$. Upon everting of the first end 11 of the tube 10, the deformation ceases to exist and the tube 10 may be fully stretched out in its circumference, thereby dilating it, such that $D1_{in} \rightarrow D2_{out}$ and $D1_{out} \rightarrow D2_{in}$. Notably, the reduction of the size of the opening of the free passage channel 19 has no negative impact on the smooth flow/outflow of substances.

Figure 8:
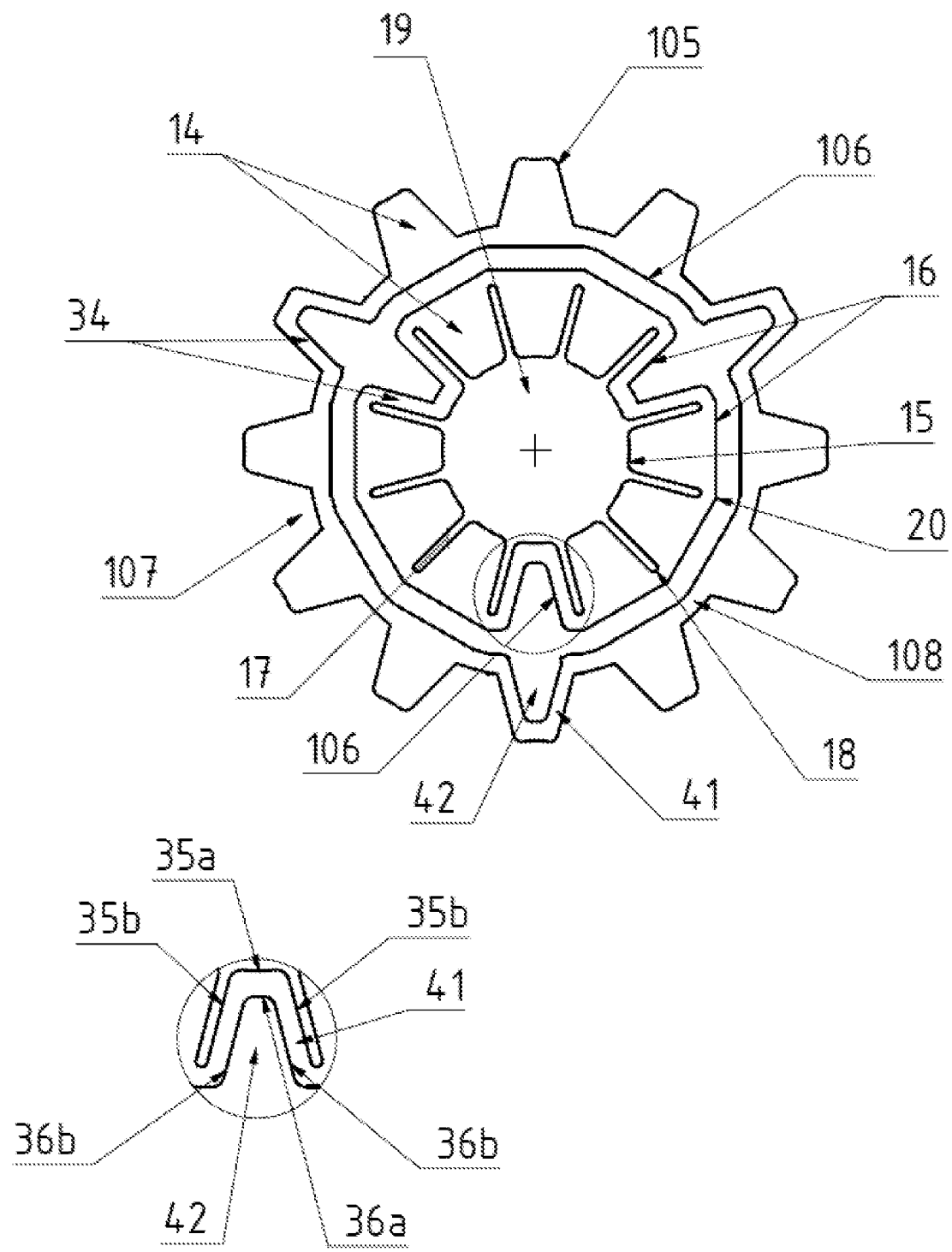
FIG. 8 shows a transversal cross-section of the catheter tube, in a configuration with dilatable protrusions according to a preferred embodiment. Both, a portion of the tube in its primary position and a portion of the tube in the everted position can be seen. A detail of the dilatable protrusion is provided.
Figure 9:
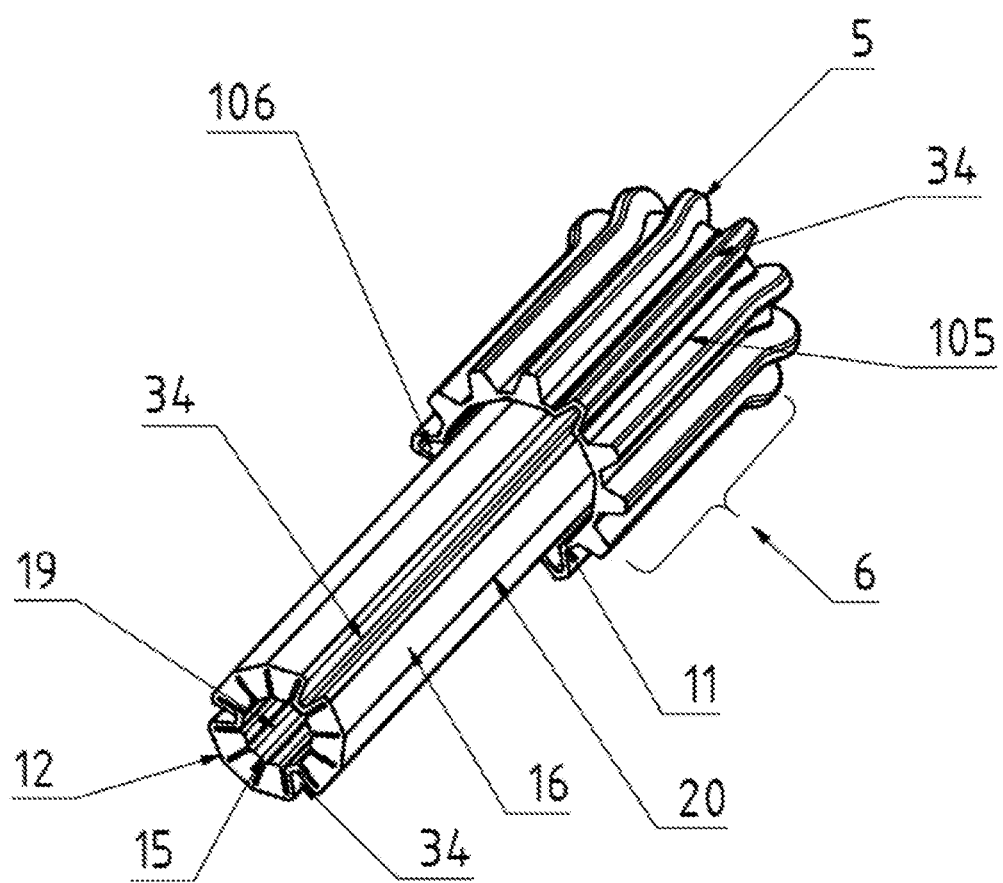
FIG. 9 shows a perspective view of the catheter tube in a configuration with dilatable protrusions according to a preferred embodiment. Both, a portion of the tube in its primary position and a portion of the tube in the everted position can be seen.

Referring to FIGS. 8 and 9, one or more of the longitudinal protrusions 14 may be replaced by the dilatable protrusions 34. The dilatable protrusions 34 may have the same size and shape as the protrusions 14. The dilatable protrusion 34 is, however, formed of a frame 41, the frame being dilatable in the lateral direction and embodying the inner space 42 of the dilatable protrusion 34. The primary inner surface 35 of the dilatable protrusion 34 comprises the top surface 35a and two side surfaces 35b. The primary inner surface 15 of the tube 10 in its primary position is thus formed be the primary inner surfaces of the protrusions 14 and of the dilatable protrusions 34. The primary outer surface 36 of the dilatable protrusion 34 comprises a bottom surface 36a and two side surfaces 36b. The primary outer surface 16 of the tube 10 in its primary position is thus formed be the primary outer surfaces of the protrusions 14 and of the dilatable protrusions 34.

Upon everting, the primary inner surfaces and primary outer surfaces of the dilatable protrusions 34 become everted outer surfaces and everted inner surfaces, respectively, in the same was as described before for longitudinal protrusions 14. The everted outer surface 105 of the tube 10 in its everted position is thus formed be the everted outer surfaces of the protrusions 14 and of the dilatable protrusions 34. The everted inner surface 106 of the tube 10 in its everted position is thus formed be the everted inner surfaces of the protrusions 14 and of the dilatable protrusions 34. As the dilatable protrusion 34 has a dilatable frame 41, the frame 41 may be stretched out upon everting of the tube 10, thus allowing the tube 10 to be fully stretched out in its circumference, thereby dilating it, such that $D1_{in} \rightarrow D2_{out}$ and $D1_{out} \rightarrow D2_{in}$.

Figure 11:
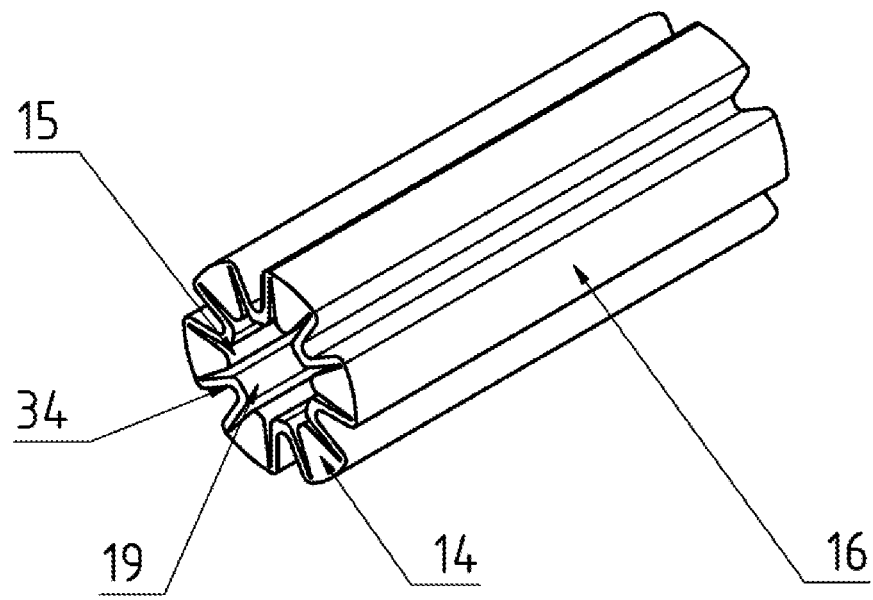
FIG. 11 shows a perspective view of the catheter tube in a configuration with longitudinal protrusions and dilatable protrusions distributed alternating along the circumference of the tube.

Referring to FIG. 11, the longitudinal protrusions 14 and dilatable protrusions 34 may be alternating along the circumference of the tube 10, such that a dilatable protrusion 34 is always positioned between two adjacent longitudinal protrusions 14. The even distribution of dilating protrusions provides the dilatation of the circumference of the catheter tube 10 upon everting, as well as reduction of the deformation of the circular shape of the tube 10 and of the free passage channel 19.

Figure 12:
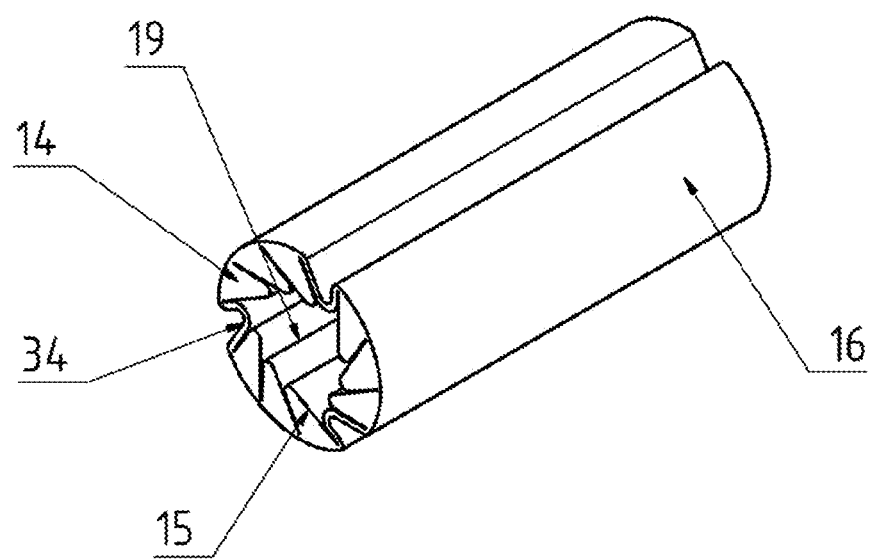
FIG. 12 shows a perspective view of the catheter tube in a configuration with longitudinal protrusions provided in a "shutter" structure.
Figure 13A:
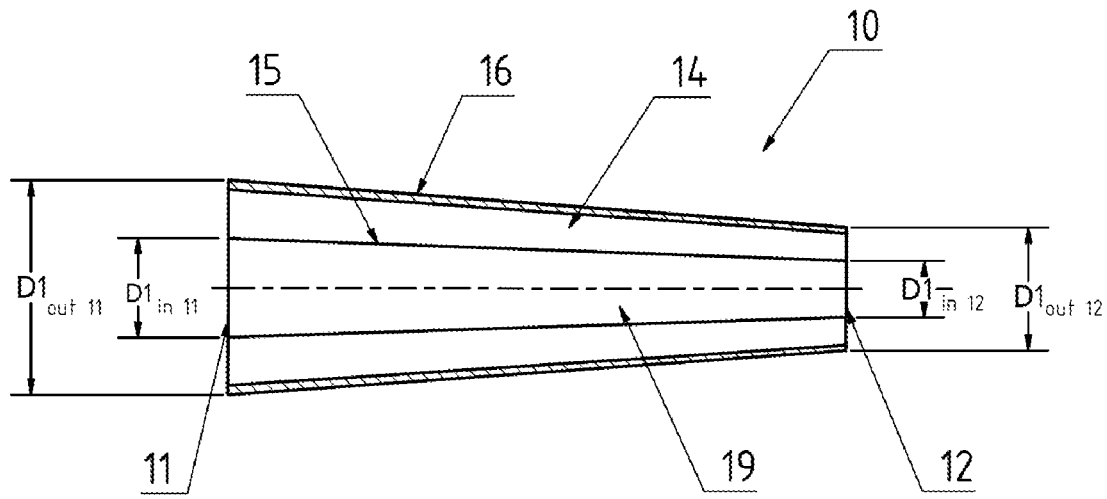
FIG. 13a shows a cross-sectional view of the catheter tube in a configuration with a tapered shape of the tube.
Figure 13B:
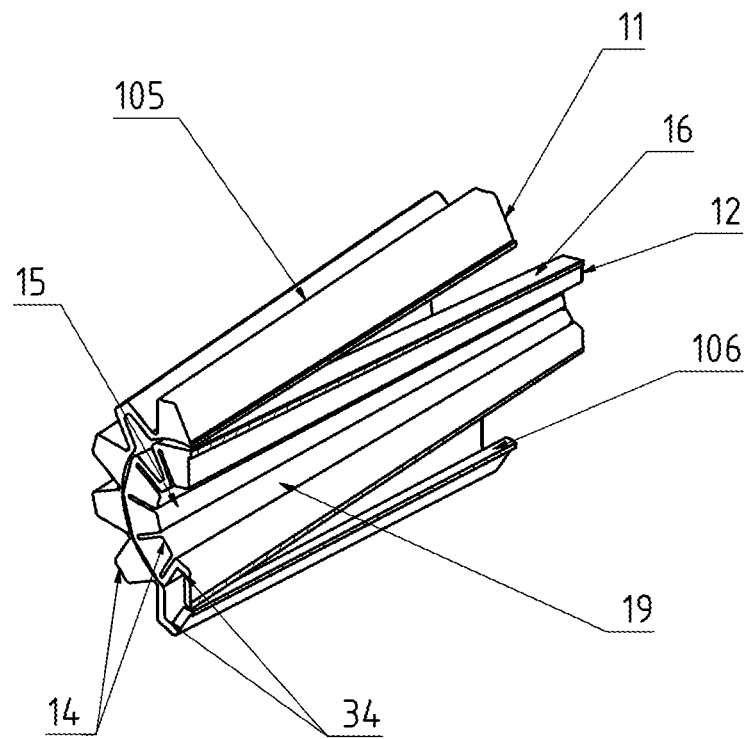
FIG. 13b shows a cross-sectional view in the everted position of the catheter tube in a configuration with a tapered shape of the tube.

Referring to FIG. 12, the longitudinal protrusions 14 and/or 34 may further be folded or inclined with respect to their normal to create a "shutter" structure.

Further, the tapered shape of the catheter tube 10 may be provided by continuous change of the diameter of the tube 10, such that the diameter of the first end 11 of the catheter tube 10—the end to be everted—is larger than the diameter of the second end 12 of the catheter tube 10 and so the everted portion of the tube has larger diameter than the non-everted portion. Thus, comparing the primary outer diameters $D1_{out}$ of the non-everted catheter tube, the primary outer diameter at the first end 11 ($D1_{out11}$) is larger than the primary outer diameter at the second end 12 ($D1_{out12}$): $D1_{out11} > D1_{out12}$. The same applies to the primary inner diameters $D1_{in11}$ and $D1_{in12}$. Thus, while the force is applied on the non-everted portion in the axial direction, and the everted portion 6 is being folded back over the non-everted portion, the difference of diameters is continuously increasing, thereby further reducing the friction between the outer surface 16 of the tube 10 in its primary position and the inner surface 106 of the everted region 6. The difference of the diameters may range from 0.1 mm up to 3 millimeters.

In a preferred embodiment, the longitudinal protrusions 14, 34 may be pre-formed during manufacture of the catheter tube 10 and expanded upon everting the catheter tube 10 inside-out.

Figure 14:
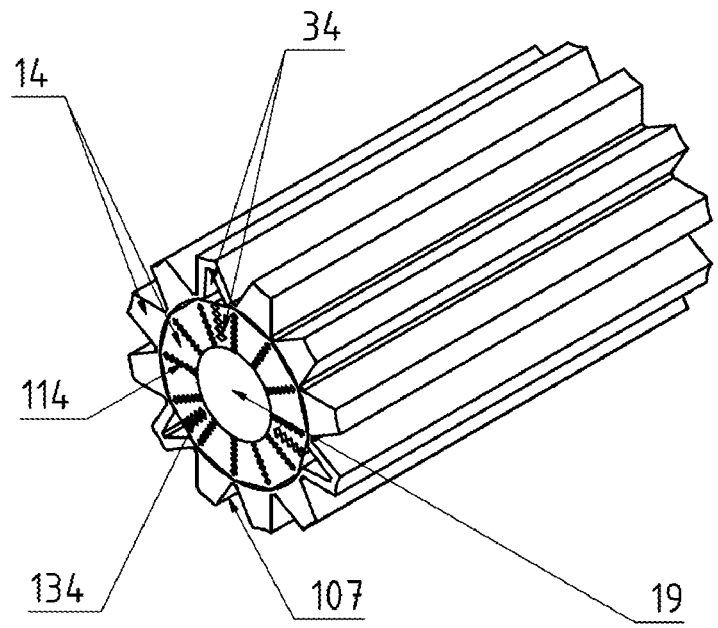
FIG. 14 shows a perspective view of the catheter tube in a configuration with longitudinal protrusions pre-formed by perforations according to a preferred embodiment.

Referring to FIG. 14, the pre-formation of the longitudinal protrusions 14, 34 may be provided by radially perforating the catheter tube 10 between the primary inner surface 15 and the primary outer surface 16 of the tube 10, such that the perforations 114 extend from the primary inner surface 15 towards the primary outer surface 16 and/or the perforations 134 extend from the primary outer surface 16 towards the primary inner surface 15 of the tube 10, depending on whether protrusions 14 or dilatable protrusions 34 are to be provided. In the case of longitudinal protrusions 14, the primary outer surface 16 shall not be perforated in order to provide the movable connection joints 18 between adjacent protrusions 14. In the case of dilatable protrusions 34, the primary inner surface 15 shall not be perforated in order to provide the dilatable frames 41 of the dilatable protrusions 34.

The perforations 114, 134 extend from the first end 11 of the tube 10 through at least part of the catheter tube 10 in its longitudinal direction. In a preferred embodiment, the length of perforations 114, 134 corresponds to at least the part of the tube 10 that is to be everted.

The perforations 114, 134 are provided at several places on the circumference of the catheter tube 10, the distance between the perforations 114 determining the width of the longitudinal protrusion 14, 34 and the number of the perforations 114 determining the number of protrusions 14, 34. The number of perforations 114 corresponds to the number of protrusions 14, 34, i.e. four perforations shall be provided for four longitudinal protrusions, twelve perforations shall be provided for twelve longitudinal protrusions, etc.

The perforations 114, 134 allow pre-forming of the longitudinal protrusions 14, 34. When the catheter 1 is to be used, and the first end 11 of the catheter tube 10 is everted, the perforations 114, 134 tear up at the fold 5 of the tube 10 upon everting and the longitudinal protrusions 14, 34 expand, such that the inter-protrusional space 107 is formed between the adjacent protrusions 14, 34, and, in case of dilatable protrusions 34, the inner space 42 embodied by the dilatable frame 41 is created.

Figure 15:
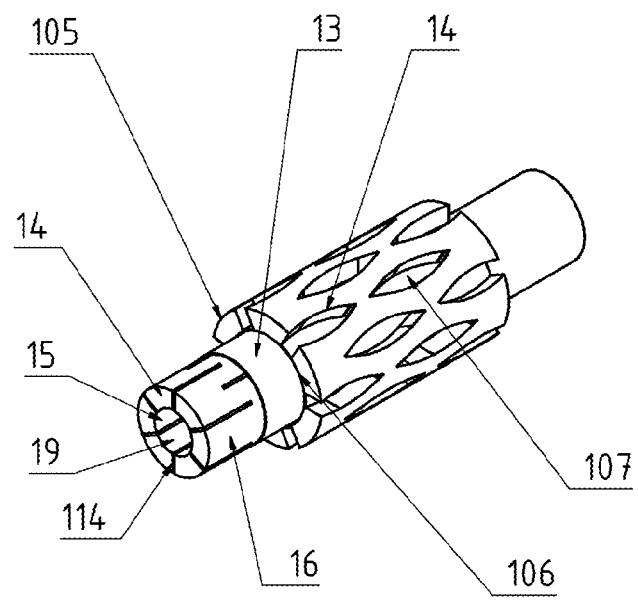
FIG. 15 shows a perspective view of the catheter tube in a configuration with longitudinal protrusions pre-formed by perforations according to a preferred embodiment.

Referring to FIG. 15, the perforations or cuts 114 may be provided discontinuously, in a structure, such that the expanded longitudinal protrusions 14 are deformed in comparison to their straight elongated shape created by continuous perforations. As the perforations 114 are provided discontinuously in this embodiment, the inter-protrusional spaces 107 formed from the perforations 114 are embodied by the protrusions 14, thereby deforming their straight elongated shape.

In this embodiment, the cuts or perforations 114 are provided over the whole thickness of the tube 10 in order to ensure full dilatation of the inter-protrusional spaces 107. In order to ensure the sterility of the interior of the catheter tube, the layer of flexible material 13 is provided.

The width and the actual shape of the protrusions 14 may be varied by varying the density, size and the distribution of the cuts or perforations 114. In a preferred embodiment, as can be seen in FIG. 15, the perforations 114 are positioned regularly, such that the perforated portions 114 and the non-perforated portions are alternating in all directions, so that each perforation 114 is positioned between two non-perforated portions in both the longitudinal and the transversal direction. The transversally adjacent perforations may overlap in the longitudinal direction over less than one half of the length of the perforation, preferably over less than one third of the length of the perforation or over less than one fourth of the length of the perforation. This mutual shift in perforations 114, and so the shift in the inter-protrusional spaces 107 provides a structure of the secondary inner surface 106, which may help to further decrease the friction between the two surfaces (16, 106) upon everting, allowing a smoother sliding. When the catheter 1 is to be used, and the first end 11 of the catheter tube 10 is everted, the cuts or perforations 114 tear up under the tension acting at the fold 5 of the tube 10 upon everting, the inter-protrusional spaces 107 are formed, and the circumference of the catheter tube 10 is dilated by dilating the created inter-protrusional spaces 107.

Furthermore, when the longitudinal protrusions 14 or 34 are inclined, creating a spiral, the tips 20 provided on the primary outer surface 16 and on the everted inner surface 106 may help to decrease the friction between the two surfaces, allowing a smoother sliding.

Any of the presented configurations may be used in combination with the layer of flexible material 13. The layer is made of material, which may be stretched out, thus allowing a dilatation of the circumference of the tube 10 upon everting, such that $D1_{in} \rightarrow D2_{out}$ and $D1_{out} \rightarrow D2_{in}$. Such a combination may further reduce the counter-forces arising at the fold 5 upon everting.

The catheter tube 10 may further be provided with a lubrication coating on its primary outer surface 16 (not shown). The lubrication coating may further reduce the friction between the primary outer surface 16 and the everted inner surface 106, thus providing a smoother sliding and smoother application of the catheter. The material used for the coating may be a lubricous hydrophilic material suitable for medical utilization, e.g. a material based on a hyaluronic acid, such as e.g. Hydak T-070. The lubrication coating may be activated with water, or during the manufacture of the tube 10. In the latter case, however, a corresponding packaging should be provided, which allows keeping the lubrication coating activated up to and for the catheterization.

In any case, for all of the configurations mentioned above, the coefficient of friction between the primary outer surface 16 and the everted inner surface 106 is less than 0.05 and less than 0.1, wherein the value of 0.1 may be considered a threshold value, because the everting becomes difficult when the coefficient of friction exceeds this threshold.

Referring to FIG. 1 again, catheter 1 of this invention may comprise additional components.

A guard 7 may be attached to the catheter tube 10. It may be located on the everted portion 6 of the tube. The guard 7 may be placed at the distance L1 from the fold 5, which is the length of the initial everted portion 6 before the catheterization. The guard 7 may have a circular shape and may surround the tube 10. The guard 7 may also have any other suitable shape, which allows keeping the catheter in its position. The guard 7 may be made of a thermoplastic material, e.g. Thermolast M of a Shore A 70 hardness, and may be manufactured by any method known in the art, for instance, a 3D printing may be used. The guard 7 may be attached to the catheter tube 10 during the manufacture, or it may be applied by the user just before the application of the catheter 1. The guard 7 may be fastened to the everted portion 6 of the tube 10 and kept in place by snap-fitting or any other way and means known in the art and suitable for medical instruments, e.g. by adhesive means.

The catheter 1 may further comprise a gripper 8 for comfortable and smoother pushing of the catheter tube 10. The gripper 8 is positioned on the catheter tube 10 and movable, or at least partly movable, between the everted first end 11 and the second end 12 of the tube 10, or between the guard 7 and a connector 9, respectively. Optionally, the guard 7 and the gripper 8 may be connected, or they may be integrally formed, thus providing a guiding channel for the catheter tube 10 and reducing, or even avoiding, the unwanted bending of the tube 10. A gripper 8 may be moved in the longitudinal direction as a whole or it may comprise extension means enabling the movement of at least a part of it. The extension means may, for instance, include a spring positioned in the longitudinal direction or a telescopic system. An electronic means for pushing the tube 10 automatically may be employed as well. Preferably, the gripper 8 may surround the tube 10, and may have a substantially cylindrical frame. The space between the catheter tube 10 and the frame of the gripper may be filled with a material, which allows, upon pressure applied by the user, to catch the tube 10 and push it in the longitudinal direction towards the first end 11 of the tube 10. Preferably, the frame of the gripper 8 may be made of a thermoplastic material, for instance of the same material as the guard 7, e.g. Thermolast M of a Shore A 70 hardness. The filling of the gripper 8 may be made of polyurethane foam. The gripper 8 may have a structured surface for comfortable placing of a user's fingers, which further improves the manipulation with the catheter 1. The gripper 8 may be applied to the catheter tube 10 during the manufacture, or it may be applied by the user just before the application of the catheter 1.

Figure 16A:
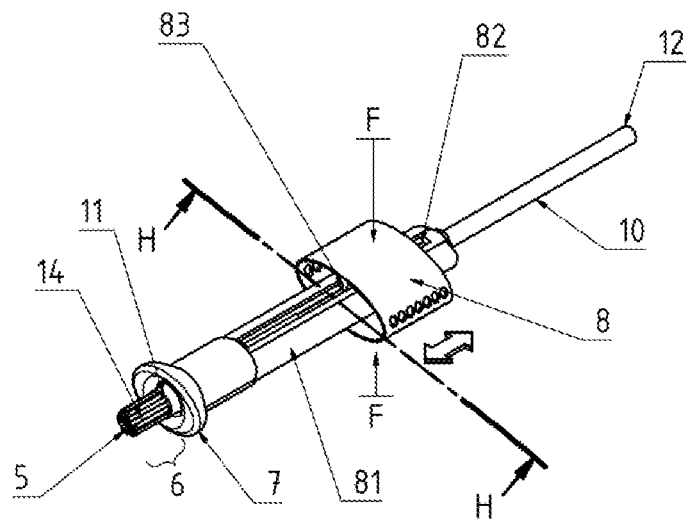
FIG. 16a shows a perspective view of a catheter in a configuration with gripper connected to the guard according to a preferred embodiment in a pre-application position.
Figure 16B:
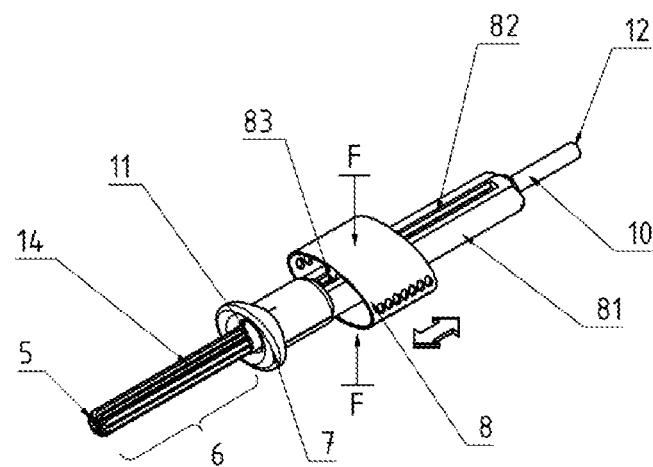
FIG. 16b shows a perspective view of a catheter in a configuration with gripper connected to the guard according to a preferred embodiment in a pre-application position in an everted position.
Figure 16C:
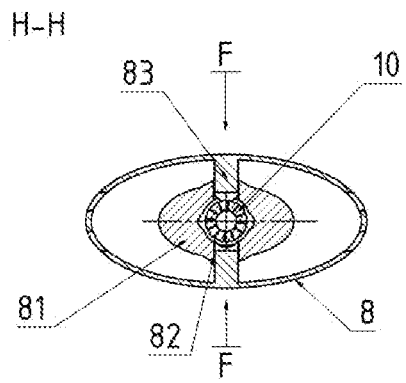
FIG. 16c shows a cross-sectional view of the gripper and the catheter tube.

Referring to FIGS. 16a, 16b, 16c a catheter 1 with a preferred configuration of the gripper 8 connected to the guard 7 may be provided by connecting the guard 7 and the gripper 8 by a longitudinal connector 81, the connector 81 surrounding the tube 10 and forming guiding channel for the catheter tube 10, such that the unwanted bending of the tube 10 (in its primary position) is eliminated. In this preferred embodiment, the longitudinal connector 81 comprises a groove 82, along which the gripper 8 is movable by means of a slider 83 inserted in the groove 82. The slider 83 may be connected to the gripper 8 or integrally formed with it. A part of the slider 83 that comes into contact with the catheter tube 10 may be provided with means for increasing friction between the slider 83 and the catheter tube 10, e.g. with polyurethane foam, rubber, teeth or any other structure. In the pre-application position (FIG. 16a) the gripper 8 is positioned at the end of the longitudinal connector 81, which is distant to the guard 7. For the application of the catheter 1, a pressure is applied by a user to the gripper 8 in the direction of the F arrows. The increased friction between the contact surface of the gripper 8 and the catheter tube 10 ensures the temporary connection between the slider 83 (and so the gripper 8) and the catheter tube 10. Thus, by pushing the gripper 8 towards the guard 7 along the groove 82, the tube 10 is pushed in the desired axial direction together with the gripper 8. The first end 11, which is proximate to the body cavity, is pre-everted and attached to the guard 7 such that its position remains unchanged during the application of the catheter 1 and, by moving the gripper 8 along the longitudinal connector 81, the portion of the tube 10 in its primary position is slidably moveable into and out of said everted region 6.

The desired length of the everted portion 6 of the catheter 1 is ensured by repeating the above-mentioned process. When the gripper 8 reaches the point close to the guard 7 (FIG. 16b), the pressure applied to the gripper 8 is released, and the gripper 8 is moved back to starting position distant to the guard 7 without applying the pressure, thus without moving the tube 10. In the starting position distant to the guard 7, the pressure is applied on the gripper 8 again, and further portion of the catheter tube 10 is everted by pushing the gripper 8 towards the guard 7.

The above-mentioned mechanism allows the catheter to be pull out of the body cavity without irritating or traumatizing the body tissue inside the cavity. The catheter tube is pull out by moving the gripper 8 along the groove 82 in opposite direction, i.e. pressing on the tube in the position close to guard 7 (FIG. 16b) and pull the gripper 8 away from the guard 7, thus pulling it together with the catheter tube. This process can be repeated until the catheter tube is safely out of the body cavity.

Referring further to FIG. 16c, the connector 81 may comprise two grooves 82, being positioned opposite to each other and the gripper 8 comprises two sliders 83, also positioned opposite to each other, such that the first slider is inserted in the first groove and the second slider is inserted in the second groove. In this embodiment that catheter tube 10 is pressed between the two opposite sliders 83 when pressure is applied on the gripper 8.

Finally, the catheter may comprise a connector 9. The connector 9 may be attached to the tube 10 at the second end 12 of the catheter tube 10. The connector 9 provides a connection between the catheter, or the inflow/outflow of the catheter tube 10, respectively, and a collection bag or any other medical instrument or equipment, which is attached to the catheter 1 through the connector 9. The connector 9 may surround the tube 10, and it may have a conical shape, a cylindrical shape or other suitable shape. Preferably, the connector 9 may be made of a thermoplastic material, for instance of the same material as the guard 7 and gripper 8, e.g. Thermolast M of a Shore A 70 hardness. The connector 9 may be any connector typically used for catheters, for instance, the connector 9 may have different colors, corresponding to the standardized color code (color indicates the size of the catheter). It may be applied during or after the manufacture of the catheter 1, but preferably before packaging and sterilization.

The catheter tube 10 of the invention may be extruded, injection molded or 3D printed—directly so that the longitudinal protrusions 14 face radially inwards. Preferably, this method may be used for the catheter tube 10 with longitudinal protrusions 14 in configuration with dilatable protrusions 34.

Alternatively, the catheter tube 10 may be produced so that in a first step, it is extruded in a position "inside-out", i.e., so that the longitudinal protrusions 14, 34 face radially outwards, and in a second step, the extruded tube is everted in its full length so that the longitudinal protrusions 14 face radially inwards. Following these two manufacture steps, the stresses arising at the fold 5 upon everting of the tube 10 are reduced, because during the catheterization process the tube 10 is in fact everted back into its natural position ("inside-out" position). In one preferred embodiment, in the second step, the extruded tube 10 is everted in part of its length (in majority of its length), but a portion of the tube 10 is left in the position where the longitudinal protrusions face radially outwards—thereby forming a pre-everted portion at the first end 11 of the tube 10. As said above, the pre-everted portion 6 may initially have at least 5 mm, preferably at least 15 mm.

In a preferred embodiment, the additional components (guard 7, gripper 8, and connector 9) may be attached to the catheter tube 10 during manufacture in the following order: the guard 7, the gripper 8 and the connector 9. Alternatively, a connector 9 may be attached to the second end 12 of the tube 10 at first and the guard 7 and the gripper 8 may be attached subsequently, for instance, directly by the user. In a preferred embodiment, the catheter may be closed in a packaging after the manufacture and may be sterilized. The sterilization may be any typical sterilization, e.g. Gamma or Ethylene Oxide sterilization, and the packaging may be any packaging suitable for the provided sterilization.

The invention claimed is:

1. A catheter tube (10) comprising
a first open end (11) and a second open end (12),
a plurality of longitudinal protrusions (14), the plurality of longitudinal protrusions (14) extending from the first end (11) of the catheter tube (10) through at least a portion of the catheter tube (10), and forming an angle of 5 degrees to 45 degrees with respect to the longitudinal axis of the catheter tube (10) and facing radially inwards, said longitudinal protrusions (14) forming a spiral structure, and
one or more dilatable protrusions (34) configured for dilating a circumference of the catheter tube (10) upon everting the catheter tube (10) inside-out from the first end (11) of the catheter tube (10).

2. The catheter tube (10) according to claim 1, wherein the longitudinal protrusions (14) are unevenly distributed on the circumference of the catheter tube (10).

3. The catheter tube (10) according to claim 1, wherein the longitudinal protrusions (14) and the dilatable protrusions (34) are distributed evenly on the circumference of the catheter tube (10), each dilatable protrusion (34) being positioned between two adjacent longitudinal protrusions (14).

4. The catheter tube (10) according to claim 1, wherein the longitudinal protrusions (14) form an inclination angle of 5-10 degrees with respect to the longitudinal axis of the catheter tube (10).

5. The catheter tube (10) according to claim 1, wherein the catheter tube (10) further comprises a lubrication coating on the primary outer surface (16) of the catheter tube (10).

6. The catheter tube (10) according to claim 1, wherein the catheter tube (10) further comprises tips (20) on the primary outer surface (16) of the catheter tube (10).

7. The catheter tube (10) according to claim 1, wherein the catheter tube (10) is tapered towards the second end (12) of the catheter tube (12).

8. The catheter tube (10) according to claim 1, wherein the catheter tube (10) comprises a pre-folded everted region (6) at the first end (11) of the catheter tube (10).

9. The catheter tube (10) according to claim 1, wherein the catheter tube (10) further comprises at least one of the additional components, the additional components being
a guard (7), the guard (7) being located on the everted region (6) at the first end (11) of the catheter tube (10),
a gripper (8), the gripper (8) being positioned on the catheter tube (10) and movable between the everted first end (11) and the second end (12) of the tube (10), and
a connector (9), the connector (9) being disposed at the second end (12) of the catheter tube (10).

10. The catheter tube (10) according to claim 9, wherein, when the catheter tube (10) comprises both the guard (7) and the gripper (8), the guard (7) and the gripper (8) are connected or integrally formed and form a guiding channel.

11. The catheter tube (10) according to claim 1, wherein at least movable contact joints (18) of the longitudinal protrusions (14, 34) are made of a material being capable of modifying its structure, preferably upon increased tension or temperature.

12. A method of manufacture of the catheter tube (10) of claim 1 comprising the steps of
   manufacturing a catheter tube (10) with longitudinal protrusions (14) facing radially outwards, said longitudinal protrusions (14) forming an angle of 5 degrees to 45 degrees with respect to the longitudinal axis of the catheter tube (10), said longitudinal protrusions (14) forming a spiral structure, and
   everting the catheter tube (10) inside-out to a position where the longitudinal protrusions (14) face radially inwards,
      preferably, the step of manufacturing of the catheter tube (10) being performed by extrusion, injection molding or 3D print.

13. A method of manufacture of the catheter tube (10) of claim 1 comprising the step of manufacturing the catheter tube (10) with longitudinal protrusions (14) facing radially inwards, preferably by extrusion, injection molding or 3D print.

14. The method of manufacture of the catheter tube (10) according to claim 12, wherein the step of manufacturing the catheter tube (10) is carried out by dip molding or vacuum forming.

15. The method of manufacture of the catheter tube (10) according to claim 13, wherein the longitudinal protrusions (14, 34) are pre-formed by means (114, 134) for pre-forming the longitudinal protrusions, preferably by cuts or perforations (114, 134).

16. The method of manufacture of the catheter tube (10) according to claim 15, wherein the means (114) for pre-forming the longitudinal protrusions (14), preferably cuts or perforations (114), are provided discontinuously, over the whole thickness of the catheter tube (10), and arranged so that each perforation (114) is positioned between two non-perforated portions in the longitudinal and in the transversal direction, and wherein the method further comprises a step of providing the layer of flexible material (13) over the primary outer surface (16) of the catheter tube (10).

17. The method of manufacture of the catheter tube (10) according to claim 12, wherein the step of manufacturing the catheter tube (10) is provided by a multi-layer extrusion, providing both the longitudinal protrusions (14) and the layer of flexible material (13).

18. The method of manufacture of the catheter tube (10) according to claim 12, wherein the method further comprises a subsequent step of coating a primary outer surface (16) of the catheter tube (10) with a lubrication material.

19. The method of manufacture of the catheter tube (10) according to claim 12, the method further comprising at least one of the following subsequent steps:
   everting a first end (11) of the catheter tube (10) inside out, creating an everted region (6) of the catheter tube (10),
   attaching a guard (7) to the everted region (6) of the catheter tube (10),
   attaching a gripper (8) to the catheter tube (10), and
   attaching a connector (9) to the second end (12) of the catheter tube (10).

\* \* \* \* \*